US012559542B2

(12) United States Patent
Sarvaiya et al.

(10) Patent No.: US 12,559,542 B2
(45) Date of Patent: Feb. 24, 2026

(54) GLYCOPROTEINS WITH ANTI-INFLAMMATORY PROPERTIES

(71) Applicant: MOMENTA PHARMACEUTICALS, INC., Titusville, NJ (US)

(72) Inventors: Hetal Sarvaiya, Foster City, CA (US); Nathaniel J. Washburn, Littleton, MA (US); Enrique Arevalo, Dorchester, MA (US); Carlos J. Bosques, Arlington, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 144 days.

(21) Appl. No.: 17/508,026

(22) Filed: Oct. 22, 2021

(65) Prior Publication Data

US 2022/0056109 A1 Feb. 24, 2022

Related U.S. Application Data

(63) Continuation of application No. 15/957,703, filed on Apr. 19, 2018, now abandoned, which is a continuation of application No. 14/416,869, filed as application No. PCT/US2013/052040 on Jul. 25, 2013, now abandoned.

(60) Provisional application No. 61/768,027, filed on Feb. 22, 2013, provisional application No. 61/676,253, filed on Jul. 26, 2012.

(51) Int. Cl.

| *G01N 31/00* | (2006.01) |
| *C07K 1/107* | (2006.01) |
| *C07K 14/435* | (2006.01) |
| *C07K 16/00* | (2006.01) |
| *C12P 21/00* | (2006.01) |
| *G01N 33/53* | (2006.01) |
| *A61K 38/00* | (2006.01) |

(52) U.S. Cl.

CPC ............ *C07K 16/00* (2013.01); *C07K 1/1077* (2013.01); *C07K 14/435* (2013.01); *C12P 21/005* (2013.01); *A61K 38/00* (2013.01); *C07K 2317/41* (2013.01); *C07K 2317/52* (2013.01); *C07K 2317/55* (2013.01)

(58) Field of Classification Search

None
See application file for complete search history.

(56) References Cited

U.S. PATENT DOCUMENTS

| 3,945,889 A | 3/1976 | Mima et al. |
| 4,258,134 A | 3/1981 | Yoshida et al. |
| 4,820,516 A | 4/1989 | Sawyer et al. |
| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Crvz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,723,583 A | 3/1998 | Seed et al. |
| 5,747,027 A | 5/1998 | Stern et al. |
| 5,753,454 A | 5/1998 | Lee |
| 5,759,823 A | 6/1998 | Wonq et al. |
| 5,807,715 A | 9/1998 | Morrison et al. |
| 5,827,721 A | 10/1998 | Stern et al. |
| 5,854,046 A | 12/1998 | Au-Young et al. |
| 5,856,143 A | 1/1999 | Nilsson |
| 5,879,912 A | 3/1999 | Roth |
| 5,945,322 A | 8/1999 | Gotschlich |
| 5,958,750 A | 9/1999 | Au-Young et al. |
| 6,030,815 A | 2/2000 | DeFrees et al. |
| 6,048,707 A | 4/2000 | Klock, Jr. |
| 6,057,110 A | 5/2000 | Au-Young et al. |
| 6,096,555 A | 8/2000 | Hermentin et al. |
| 6,132,994 A | 10/2000 | Tawada et al. |
| 6,156,547 A | 12/2000 | Roth |
| 6,159,954 A | 12/2000 | Maruyama et al. |
| 6,180,370 B1 | 1/2001 | Queen et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |

(Continued)

FOREIGN PATENT DOCUMENTS

| AU | 2018207367 B2 | 2/2024 |
| CA | 2828905 | 9/2012 |

(Continued)

OTHER PUBLICATIONS

Sybille Bohm et al. (Seminars in Immunopathology, vol. 34, No. 3, Mar. 22, 2012, pp. 443-453). (Year: 2012).*

Barb et al. (American Chemical Society of Biochemistry, Vo.48, No. 41, Oct. 20, 2009, pp. 9705-9707). (Year: 2009).*

Anthony et al. (Ann. N.Y. Acad. Sci. vol. 1253, 2010, pp. 170-180). (Year: 2010).*

Weikert et al. (Nature Biotechnology, vol. 17, Nov. 1999, pp. 1116-1121). (Year: 1999).*

"Glycosylation main approval issue with biosimilars," <http://gabionline.net/Conferences/Glycosylation-main-approval-issue-with-biosimilars>, dated Jan. 9, 2009, retrieved Jul. 18, 2016 (2 pages).

(Continued)

*Primary Examiner* — Lisa V Cook

(74) *Attorney, Agent, or Firm* — Morgan, Lewis & Bockius LLP

(57) ABSTRACT

Glycoproteins having particular sialylation patterns, and methods of making and using such glycoproteins, are described.

15 Claims, 4 Drawing Sheets

Specification includes a Sequence Listing.

(56) References Cited

U.S. PATENT DOCUMENTS

| | | | |
|---|---|---|---|
| 6,280,989 | B1 | 8/2001 | Kapitonov et al. |
| 6,284,516 | B1 | 9/2001 | Pollock et al. |
| 6,358,710 | B1 | 3/2002 | Graves et al. |
| 6,399,336 | B1 | 6/2002 | Bayer et al. |
| 6,597,996 | B1 | 7/2003 | Venkataraman et al. |
| 6,946,075 | B2 | 9/2005 | Kopf |
| 7,118,675 | B2 | 10/2006 | An et al. |
| 7,138,120 | B2 | 11/2006 | Laursen et al. |
| 7,364,736 | B2 | 4/2008 | Boyle et al. |
| 7,368,542 | B2 | 5/2008 | McIntyre |
| 7,465,397 | B2 | 12/2008 | An et al. |
| 7,473,680 | B2 | 1/2009 | Bowe et al. |
| 7,655,233 | B2 | 2/2010 | Autenreith et al. |
| 7,767,429 | B2 | 8/2010 | Bookbinder et al. |
| 7,829,081 | B2 | 11/2010 | Bookbinder et al. |
| 7,846,431 | B2 | 12/2010 | Bookbinder et al. |
| 7,871,607 | B2 | 1/2011 | Bookbinder et al. |
| 8,034,906 | B2 | 10/2011 | Borhani et al. |
| 8,105,586 | B2 | 1/2012 | Bookbinder et al. |
| 8,187,855 | B2 | 5/2012 | Baker et al. |
| 8,278,072 | B1 | 10/2012 | Matta et al. |
| 8,524,217 | B2 | 9/2013 | Presta et al. |
| 8,546,548 | B2 | 10/2013 | Bauer et al. |
| 8,632,773 | B2 | 1/2014 | Elkon et al. |
| 8,715,652 | B2 | 5/2014 | Bolli et al. |
| 8,772,461 | B2 | 7/2014 | Earp et al. |
| 8,932,825 | B2 | 1/2015 | Wildt |
| 9,114,179 | B2 | 8/2015 | Zhang et al. |
| 9,127,043 | B2 | 9/2015 | Gronke et al. |
| 9,170,249 | B2 * | 10/2015 | Washburn ............. C12P 21/005 |
| 9,175,068 | B2 | 11/2015 | Bauer et al. |
| 9,217,168 | B2 | 12/2015 | Prentice |
| 9,481,902 | B2 | 11/2016 | Czabany et al. |
| 9,637,768 | B2 | 5/2017 | Choi et al. |
| 9,663,581 | B2 | 5/2017 | Washburn et al. |
| 9,725,501 | B2 | 8/2017 | Earp et al. |
| 9,809,835 | B2 | 11/2017 | Engel |
| 9,890,410 | B2 * | 2/2018 | Washburn ............. C07K 16/00 |
| 10,087,236 | B2 | 10/2018 | Wong et al. |
| 10,125,189 | B2 | 11/2018 | Bauer et al. |
| 10,287,315 | B2 | 5/2019 | Choi et al. |
| 10,344,063 | B2 | 7/2019 | Huang et al. |
| 10,464,996 | B2 | 11/2019 | Prod'Homme et al. |
| 10,668,411 | B2 | 6/2020 | Lu et al. |
| 10,836,805 | B2 | 11/2020 | Huang et al. |
| 11,078,511 | B2 | 8/2021 | Greif et al. |
| 11,098,079 | B2 | 8/2021 | Gonzalez et al. |
| 11,352,415 | B2 | 6/2022 | Prod'Homme |
| 11,377,485 | B2 | 7/2022 | Wong et al. |
| 11,661,456 | B2 | 5/2023 | Schultes |
| 2002/0054878 | A1 | 5/2002 | Lowman et al. |
| 2003/0157108 | A1 | 8/2003 | Presta |
| 2004/0137106 | A1 | 7/2004 | Ciccone |
| 2004/0138106 | A1 | 7/2004 | Schultz et al. |
| 2004/0210396 | A1 | 10/2004 | Fischer et al. |
| 2005/0054832 | A1 | 3/2005 | Lazar et al. |
| 2005/0106658 | A1 | 5/2005 | Bayer et al. |
| 2006/0030521 | A1 | 2/2006 | Bayer et al. |
| 2006/0040353 | A1 | 2/2006 | Davidson et al. |
| 2006/0127950 | A1 | 6/2006 | Bosques et al. |
| 2006/0252672 | A1 | 11/2006 | Betenbaugh et al. |
| 2006/0253928 | A1 | 11/2006 | Bakker et al. |
| 2008/0261301 | A1 | 10/2008 | Kanda et al. |
| 2009/0041770 | A1 | 2/2009 | Chamberlain et al. |
| 2009/0053238 | A1 | 2/2009 | Allan |
| 2009/0069232 | A1 | 3/2009 | Callewaert et al. |
| 2009/0104603 | A1 | 4/2009 | Satomaa et al. |
| 2009/0203550 | A1 | 8/2009 | Venkataraman et al. |
| 2009/0226968 | A1 | 9/2009 | Betenbaugh et al. |
| 2009/0252749 | A1 | 10/2009 | Leister et al. |
| 2009/0258014 | A1 | 10/2009 | Laterra et al. |
| 2009/0304665 | A1 | 12/2009 | Bilinsky et al. |
| 2009/0311732 | A1 | 12/2009 | Rossi et al. |
| 2009/0317834 | A1 | 12/2009 | Laine et al. |
| 2010/0048456 | A1 | 2/2010 | DeFrees et al. |

| | | | |
|---|---|---|---|
| 2010/0074885 | A1 | 3/2010 | Schiff et al. |
| 2010/0081150 | A1 | 4/2010 | Liu et al. |
| 2010/0113294 | A1 | 5/2010 | Venkataraman et al. |
| 2010/0129843 | A1 | 5/2010 | Parsons et al. |
| 2010/0136599 | A1 | 6/2010 | Gandhe et al. |
| 2010/0143969 | A1 | 6/2010 | Schwartz et al. |
| 2010/0144553 | A1 | 6/2010 | Bosques et al. |
| 2010/0166774 | A1 | 7/2010 | Dali et al. |
| 2010/0173323 | A1 | 7/2010 | Strome et al. |
| 2010/0189714 | A1 | 7/2010 | Ravetch et al. |
| 2010/0240871 | A1 | 9/2010 | Raju et al. |
| 2010/0278808 | A1 | 11/2010 | Ravetch et al. |
| 2011/0008309 | A1 | 1/2011 | Bookbinder et al. |
| 2011/0053247 | A1 | 3/2011 | Baker et al. |
| 2011/0076277 | A1 | 3/2011 | Ravetch et al. |
| 2011/0224102 | A1 | 9/2011 | Gray et al. |
| 2011/0263828 | A1 | 10/2011 | Wong et al. |
| 2011/0280873 | A1 | 11/2011 | Presta et al. |
| 2012/0009189 | A1 | 1/2012 | Kasermann et al. |
| 2012/0058111 | A1 | 3/2012 | Ehlers et al. |
| 2012/0100575 | A1 | 4/2012 | Taylor et al. |
| 2012/0101325 | A1 | 4/2012 | Lee et al. |
| 2012/0295273 | A1 | 11/2012 | Washburn et al. |
| 2013/0121991 | A1 | 5/2013 | Sylvain et al. |
| 2013/0216522 | A1 | 8/2013 | Huille et al. |
| 2015/0087814 | A1 | 3/2015 | Wang et al. |
| 2015/0210753 | A1 | 7/2015 | Sarvaiya et al. |
| 2015/0252108 | A1 | 9/2015 | Washburn et al. |
| 2016/0090409 | A1 | 3/2016 | Prod'Homme et al. |
| 2016/0102298 | A1 | 4/2016 | Czabany et al. |
| 2016/0108450 | A1 | 4/2016 | Bhatnager et al. |
| 2016/0153020 | A1 | 6/2016 | Ronin |
| 2016/0257754 | A1 | 9/2016 | Schultes et al. |
| 2017/0320959 | A1 | 11/2017 | Swanson et al. |
| 2018/0186847 | A1 | 7/2018 | Wang et al. |
| 2018/0305440 | A1 | 10/2018 | Sarvaiya et al. |
| 2018/0305725 | A1 | 10/2018 | Bhatnager et al. |
| 2018/0327498 | A1 | 11/2018 | Schultes et al. |
| 2019/0002542 | A1 | 1/2019 | Li et al. |
| 2019/0085064 | A1 | 3/2019 | Bauer et al. |
| 2019/0100573 | A1 | 4/2019 | Wong et al. |
| 2019/0161533 | A1 | 5/2019 | Hannappel et al. |
| 2019/0194303 | A1 | 6/2019 | Wong et al. |
| 2019/0271021 | A1 | 9/2019 | Kopetzki et al. |
| 2020/0032312 | A1 | 1/2020 | Bhatnager et al. |
| 2020/0055921 | A1 | 2/2020 | Homme et al. |
| 2020/0087298 | A1 | 3/2020 | Bechtold et al. |
| 2020/0087402 | A1 | 3/2020 | Schultes et al. |
| 2021/0017563 | A1 | 1/2021 | Bhatnager et al. |
| 2021/0040527 | A1 | 2/2021 | Bhatnager et al. |
| 2021/0163531 | A1 | 6/2021 | Abel et al. |
| 2021/0277438 | A1 | 9/2021 | Bhatnager et al. |
| 2021/0353752 | A1 | 11/2021 | Arroyo et al. |
| 2022/0056109 | A1 | 2/2022 | Bosques et al. |
| 2022/0267413 | A1 | 8/2022 | Bosques et al. |

FOREIGN PATENT DOCUMENTS

| | | | |
|---|---|---|---|
| CN | 110100007 | A | 8/2019 |
| EP | 0798003 | | 10/1997 |
| EP | 1038881 | | 9/2000 |
| EP | 2233502 | | 9/2010 |
| EP | 2271382 | | 1/2011 |
| EP | 2403866 | | 1/2012 |
| EP | 2821482 | A1 | 1/2015 |
| EP | 2996772 | | 3/2016 |
| EP | 3004368 | | 4/2016 |
| EP | 3017057 | | 5/2016 |
| EP | 3118209 | | 1/2017 |
| EP | 3237608 | | 11/2017 |
| JP | 2002-542787 | | 12/2002 |
| JP | 2005-509403 | | 4/2005 |
| JP | 2009055837 | | 3/2009 |
| JP | 2013527761 | A | 7/2013 |
| JP | 2013534540 | | 9/2013 |
| JP | 2013537546 | A | 10/2013 |
| JP | 2016-523539 | A | 8/2016 |
| JP | 2019-514361 | A | 6/2019 |
| JP | 2020501581 | A | 1/2020 |

(56)　　References Cited

FOREIGN PATENT DOCUMENTS

| KR | 1020130119904 | | 11/2013 |
|---|---|---|---|
| KR | 101667677 | B1 | 10/2016 |
| NZ | 597651 | A | 7/2012 |
| RU | 2580045 | C2 | 4/2016 |
| RU | 2698655 | C2 | 8/2019 |
| RU | 2714209 | C2 | 2/2020 |
| WO | WO 92/22324 | | 12/1992 |
| WO | WO1998/031826 | | 7/1998 |
| WO | WO 98/46645 | | 10/1998 |
| WO | WO 99/64462 | | 12/1999 |
| WO | WO 00/65070 | | 11/2000 |
| WO | WO 01/80884 | | 11/2001 |
| WO | WO 02/00879 | | 1/2002 |
| WO | WO 02/30954 | | 4/2002 |
| WO | WO 02/076578 | | 10/2002 |
| WO | WO2005049078 | A2 | 6/2005 |
| WO | WO 2005/116221 | | 12/2005 |
| WO | WO2007/005786 | | 1/2007 |
| WO | WO 2007/011041 | | 1/2007 |
| WO | WO2007/019232 | | 2/2007 |
| WO | WO 2007/055916 | | 5/2007 |
| WO | WO 2007/076032 | | 7/2007 |
| WO | WO 2007/087384 | | 8/2007 |
| WO | WO 2007/117505 | | 10/2007 |
| WO | WO 2008/057634 | | 5/2008 |
| WO | WO 2008/063982 | | 5/2008 |
| WO | WO 2008/128216 | | 10/2008 |
| WO | WO 2008/128218 | | 10/2008 |
| WO | WO 2008/128219 | | 10/2008 |
| WO | WO 2008/128220 | | 10/2008 |
| WO | WO 2008/128221 | | 10/2008 |
| WO | WO 2008/128222 | | 10/2008 |
| WO | WO 2008/128225 | | 10/2008 |
| WO | WO 2008/128227 | | 10/2008 |
| WO | WO 2008/128228 | | 10/2008 |
| WO | WO 2008/128230 | | 10/2008 |
| WO | WO 2008/130924 | | 10/2008 |
| WO | WO 2008/130926 | | 10/2008 |
| WO | WO 2009/021708 | | 2/2009 |
| WO | WO 2009/058564 | | 5/2009 |
| WO | WO 2009/079382 | | 6/2009 |
| WO | WO2009/111240 | | 9/2009 |
| WO | WO 2010/071817 | | 6/2010 |
| WO | WO 2010/071824 | | 6/2010 |
| WO | WO 2010/085251 | | 7/2010 |
| WO | WO 2010/130756 | | 11/2010 |
| WO | WO 2010/136492 | | 12/2010 |
| WO | WO 2010/138502 | | 12/2010 |
| WO | WO2010/138736 | | 12/2010 |
| WO | WO 2010/141855 | | 12/2010 |
| WO | WO 2011/069056 | | 6/2011 |
| WO | WO 2011/103584 | | 8/2011 |
| WO | WO 2011/127322 | | 10/2011 |
| WO | WO 2011/127325 | | 10/2011 |
| WO | WO2011/138391 | A1 | 11/2011 |
| WO | WO2011157950 | A1 | 12/2011 |
| WO | WO2012/022814 | A1 | 2/2012 |
| WO | WO 2012/113863 | | 8/2012 |
| WO | WO 2012/120125 | | 9/2012 |
| WO | WO2013/087992 | | 6/2013 |
| WO | WO 2013/120066 | | 8/2013 |
| WO | WO 2014/018747 | | 1/2014 |
| WO | WO 2014/052360 | | 4/2014 |
| WO | WO2014055370 | A1 | 4/2014 |
| WO | WO 2014/179601 | | 11/2014 |
| WO | WO2014184545 | A1 | 11/2014 |
| WO | WO2014186310 | A1 | 11/2014 |
| WO | WO 2015/001033 | | 1/2015 |
| WO | WO2015/001034 | A1 | 1/2015 |
| WO | WO 2015/057622 | | 4/2015 |
| WO | WO2017/181148 | A2 | 10/2017 |
| WO | WO2018/046774 | | 3/2018 |
| WO | WO2018/114878 | | 6/2018 |
| WO | WO2018114878 | A1 | 6/2018 |
| WO | WO2018/131893 | | 7/2018 |
| WO | WO2019/0126041 | A1 | 6/2019 |
| WO | WO2020/077298 | A1 | 4/2020 |
| WO | WO2020077298 | A9 | 5/2020 |
| WO | WO2020/215021 | | 10/2020 |
| WO | WO2021/236765 | | 11/2021 |
| WO | WO2022/038565 | A1 | 2/2022 |

OTHER PUBLICATIONS

"Scientific Considerations in Demonstrating Biosimilarity to a Reference Product: Guidance for Industry," Food and Drug Administration (2012) (25 pages).

Afonso et al., "The Production Processes and Biological Effects of Intravenous Immunoglobulin," Biomolecules, 2016, 6(15):1-20.

Ahn et al., "Separation of 2-aminobenzamide labeled glycans using hydrophilic interaction chromatography columns packed with 1.7 (mu)m sorbent," J Chromatoqr. 878(3-4):403-8 (2010).

Akiyama et al., "Analysis of the role of glycosylation of the human fibronectin receptor", J. Biol. Chem. vol. 264(30):18011-8 (1989).

Alfthan et al., "Properties of a single-chain antibody containing different linker peptides ," Protein Eng., 1995, 8:725-731.

Andrade et al., "Solid-phase oligosaccharide synthesis: preparation of complex structures using a novel linker and different glycosylating agents", Org Lett. 1 (11): 1811-4 (1999).

Anthony et al., "A Recombinant IgG Fc That Recapitulates the Antiinflammatory Activity of IVIG," Science, Apr. 2008, 320(5874):373-376.

Anthony et al., "Identification of a receptor required for the anti-inflammatory activity of IVIG." Proc Natl Acad Sci USA. 105(50):19571-8 (2008).

Anthony et al., "Intravenous gammaglobulin suppresses inflammation through a novel TH2 pathway." Nature. 475(7354):110-3 (2011) (5 pages).

Anthony et al., "Novel roles for the IgG Fc glycan," Ann NY Acad Sci. 1253(2012):170-80 (2012).

Anthony et al., "Recapitulation of IVIG anit-inflammatory activity with a recombinant IgG Fc." Science. 320(5874):373-6 (2008).

Anthony et al., "Supporting Online Material for Recapitulation of IVIG anti-inflammatory activity with a recombinant IaG Fc," Science. 320: 9 pages (2008).

Anthony et al., "A novel role for the IgG Fc glycan: the anti-inflammatory activity of sialylated IgG Fcs," J Clin Immunol. 30(Suppl 1):9-14 (2010).

Anumula, "Advances in fluorescence derivatization methods for high-performance liquid chromatographic analysis of glycoprotein carbohydrates", Anal Biochem. 350(1):1-23 (2006).

Anumula, "Quantitative glycan profiling of normal human plasma derived immunoglobulin and its fragments Fab and Fc," J. Immunol. Methods., 2012, 382:167-176.

Arnold et al., "Human Serum IgM Glycosylation: Identification of Glycoforms That Can Bind To Mannan-Binding Lectin," J. Biol. Chem., 2005, 280:29080-29087.

Arumugam et al., "Intravenous immunoglobulin (IVIG) protects the brain against experimental stroke by preventing complement-mediated neuronal cell death," Procd Natl Acd Sci., 2007, 104(35):14101-14109.

Baker et al., "Metabolic control of recombinant protein N-glycan processing in NSO and CHO cells", Biotechnol Bioeng. 73(3):188-202 (2001).

Barb et al., "Branch specific sialylation of IgG-Fc Glycans by ST6Gal-I." Biochemistry. 48(41):9705-7 (2009) (6 pages).

Barb et al., "NMR characterization of immunoglobulin G Fc glycan motion on enzymatic sialylation." Biochemistry. 51 (22):4618-26 (2012).

Barb et al., Supporting Information for "Branch specific sialylation of IgG-Fc Glycans by ST6Gal-I," Biochemistry. 48(41):9705-7 (2009) (8 paaes).

Barsam et al., "Platelet production and platelet destruction: assessing mechanisms of treatment effect in immune thrombocytopenia", Blood, 2011, 117(21):5723-5732.

Becker et al., "Fucose: biosynthesis and biological function in mammals," Glycobiology. 13(7):41 R-53R (2003).

(56) References Cited

OTHER PUBLICATIONS

Bohm et al., "The role of sialic acid as a modulator of the anti-inflammatory activity of IgG," Semin Immunopathol. 34(3):443-53 (2012).

Bohne et al., "Sweet—WWW-based rapid 30 construction of oligo- and polysaccharides", Bioinformatics. 15(9): 767-768 (1999).

Bollati-Fogolin et al., "Temperature reduction in cultures of hGM-CSF-expressing CHO cells: effect on productivity and product quality", Biotechnol Prog. 21 (1 ):17-21 (2005).

Bork et al., "Increasing the sialylation of therapeutic glycoproteins: The potential of the sialic acid biosynthetic pathway," J. Pharm. Sci, 2009, 98:3499-3508.

Bowman et al., "Biosynthesis of L-selectin ligands: sulfation of sialyl Lewis x-related oligosaccharides by a family of GlcNAc-6-sulfotransferases", Biochemistry. 40(18):5382-91 (2001).

Breidenbach et al., "Targeted metabolic labeling of yeast N-glycans with unnatural sugars," Proc Natl Acad Sci USA. 107(9):3988-93 (2010).

Brinkman et al., "Phage display of disulfide-stabilized Fv fragments," J Immunol Methods., 1995, 182:41-50.

Broschat et al., "Purification and characterization of GDP-D-mannose 4,6-dehydratase from porcine thyroid", Eur J Biochem. 153(2):397-401 (1985).

Cabrera et al., "Influence of culture conditions on the N-glycosylation of a monoclonal antibody specific for recombinant hepatitis B surface antigen", Biotechnol Appl Biochem. 41(Pt1):67-76 (2005).

Campbell et al., "Therapeutic Effect of IVIG on Inflammatory Arthritis in Mice is Dependent on the Fc Portion and Independent of Sialylation or Basophils," J of Immunology., Jun. 1, 2014, 192 (11) 5031-5038.

Candore et al., "Inflammation, Cytokines, Immune Response, Apolipoprotein E, Cholesterol, and Oxidative Stress in Alzheimer Disease: Therapeutic Implications," Rejuvenation Research, 2010, 13(2-3):301-313.

Carpenter et al., "Potential inaccurate quantitation and sizing of protein aggregates by size exclusion chromatography: Essential need to use orthogonal methods to assure the quality of therapeutic protein products," J. Pharm. Sci., 2010, 99:2200-2208.

CAS No. 9007-83-4, "γ-Globulins from human blood," retrieved Apr. 5, 2021, retrieved from URL <https://www.sigmaaldrich.com/catalog/product/sigma/g4386?lang-en®ion=US>, 3 pages.

Chelius et al., "Formation of pyroglutamic acid from n-terminal glutamic acid in immunoglobulin gamma antibodies," Anal Chem. 78:2370-6 (2006).

Chen & Colley, "Minimal structural and glycosylation requirements for ST6Gal I activity and trafficking" Glycobiology, 2000, 10:531-538.

Chen et al., "Analysis of N-glycans from recombinant immuno-globulin G by on-line reversedphase high-performance liquid chromatography/mass spectrometry," Anal Biochem. 370:147-61 (2007).

Chen et al., "Effects of elevated ammonium on glycosylation gene expression in CHO cells", Metab Enq. 8(2):123-32 (2006).

Chen et al., "Gas-phase oligosaccharide nonreducing end (GONE) sequencing and structural analysis by reversed phase HPLC/mass spectrometry with polarity switching, " J Am Soc Mass Spectrom. 20:1821-33 (2009).

Chen et al., "Independent Lec1A CHO glycosylation mutants arise from point mutations in Nacetylglucosaminyltransferase I that reduce affinity for both substrates. Molecular consequences based on the crystal structure of GlcNAc-TI", Biochemistry. 40(30):8765-72 (2001 ).

Chen et al., "T cell receptor signaling co-regulates multiple Golgi genes to enhance N-glycan branching," J Biol Chem. 284(47):32454-61 (2009).

Cheng, et al., "Trans-sialidase activity of Photobacterium damsela α2,6-sialyltransferase and its application in the synthesis of sialosides," Glycobiology, 2010, 20:260-268.

Chumsae et al., "Identification and localization of unpaired cysteine residues in monoclonal antibodies by fluorescence labeling and mass spectrometry," Anal Chem. 81 (15):6449-57 (2009).

Clark et al., "Gene-expression profiles for five key glycosylation genes for galactose-fed CHO cells expressing recombinant IL-4/13 cytokine trap", Biotechnol Bioeng. 90(5):568-77 (2005).

Coisne et al., "Cutting edge: Natalizumab blocks adhesion but not initial contact of human T cells to the blood-brain barrier in vivo in an animal model of multiple sclerosis, " J Immunol., 2009, 182:5909-5913.

Communication pursuant to Article 94(3) EPC for European Application No. 13822833.3, dated Aug. 31, 2017 (7 pages).

Communication pursuant to Article 94(3) EPC for European Patent Application No. 14792116.7, dated Jul. 25, 2017 (6 pages).

Communication Pursuant to Article 94(3) in European Application No. 14792116.7, dated Mar. 12, 2018, 5 pages.

Communication Pursuant to Article 94(3) in European Application No. 13822833.3, dated Feb. 18, 2021, 4 pages.

Communication Pursuant to Article 94(3) in European Application No. 13822833.3, Jan. 21, 2020, 4 pages.

Communication Pursuant to Article 94(3) in European Application No. 13822833.3, Nov. 29, 2018, 4 pages.

Communication Pursuant to Article 94(3) in European Application No. 14792116.7, dated Dec. 17, 2018, 5 pages.

Communication Pursuant to Article 94(3) in European Application No. 14853244.3, dated Jan. 14, 2021, 5 pages.

Communication Pursuant to Article 94(3) in European Application No. 14853244.3, dated Jul. 19, 2019, 7 pages.

Cooper et al., "GlycoSuiteDB: a curated relational database of glycoprotein glycan structures and their biological sources. 2003 update", Nucleic Acids Res. 31 (1):511-3 (2003).

Cooper et al., "GlycoSuiteDB: a new curated relational database of glycoprotein glycan structures and their biological sources," Nucleic Acids Res. 29(1):332-5 (2001).

Cox et al., "Glycan optimization of a human monoclonal antibody in the aquatic plant Lemna minor", Nat Biotechnol. 24(12):1591-7 (2006).

Crowell et al., "Amino acid and manganese supplementation modulates the glycosylation state of erythropoietin in a CHO culture system", Biotechnol Bioeng. 96(3):538-549 (2007) (29 pages).

Cummings et al., "Antibodies and Lectins in Glycan Analysis." Essentials of Glycobiology. Varki A, Cumminas RD, Eska JD et al., 1-17 (2009).

Czajkowsky et al., "Fc-fusion proteins: new developments and future perspectives," EMBO Mol. Med, 2012, 4:1015-1028.

Debray et al., Glycoprotein Analysis: General Methods. Encyclopedia of Analytical Chemistry. John Wiley & Sons, 1-39 (2006).

Dick et al., "C-terminal lysine variants in fully human monoclonal antibodies: investigation of test methods and possible causes," Biotechnol Bioenq. 100(6):1132-43 (2008).

Donaldson et al., "The use of lectins to select subpopulations of insect cells", Biotechnol Bioeng. 64(5):616-9 (1999).

Dorka, Penny, Thesis: "Modelling Batch and Fed-Batch Mammalian Cell Cultures for Optimizing MAb Productivity," Master of Science, University of Waterloo, 2007 (197 pages).

Dos Santos et al., "Kinin B2 receptor regulates chemokines CCL2 and CCL5 expression and modulates leukocyte recruitment and pathology in experimental autoimmune encephalomyelitis (EAE) in mice," J Neuroinflammation., Nov. 2008, 5:49.

Drecktrah et al., "Inhibition of a Golgi complex lysophospholipid acyltransferase induces membrane tubule formation and retrograde trafficking," Mal Biol Cell. 14(8):3459-69 (2003).

Durandy et al. "Immunoglobulin replacement therapy in primary antibody deficiency 1-16, 19-48, 51-53 diseases—maximizing success," Int Arch Allergy Immunol., Feb. 15, 2005, 136(3):217-229.

Dwyer, "Manipulating the immune system with immune globulin," N Engl J Med. 326(2):107-16 (1992).

El Khoury et al., "Ccr2 deficiency impairs microglial accumulation and accelerates progression of Alzheimer-like disease," Nat Med., 2007, 13:432-438.

Engel et al., "Rec. ST6Gal-I variants to control enzymatic activity in processes of in vitro glycoengineering," BMC Proceedings, (Suppl 6):P110 (2013).

Extended European Search Report for European Application No. 13822833.3, dated Jun. 6, 2016 (9 pages).

(56) References Cited

OTHER PUBLICATIONS

Extended European Search Report for European Application No. 14792116. 7, dated Oct. 21, 2016 2016 (9 paqes).

Extended European Search Report for European Application No. 14798473.6, dated Oct. 13, 2016 (10 pages).

Extended European Search Report for European Application No. 14853244.3, mailed Jun. 8, 2017 (11 pages).

Extended European Search Report for European Application No. 20158041.2, dated Sep. 9, 2020 (9 pages).

Fareed, "S-9-10 synthetic and biotechnology derived glycomimetics. Impact on drug development", Abstract of 6th Proteoglycan Forum, Jun. 24, Hamamatsu, Japan (2000) (1 page).

Feasby et al., "Guidelines on the use of intravenous immune globulin for neurologic conditions," Transfus Med Rev. 21 (2 Suppl 1):S57-107 (2007).

Ferrara et al., "Modulation of therapeutic antibody effector functions by glycosylation engineering: influence of golgi enzyme localization domain and co-expression of heterologous beta1, 4-N-acetylglucosaminyltransferase III and golgi alpha-mannosidase II," Biotechnol Bioeng. 93(5):851-861 (2006).

Fitz et al., "Combined use of subtilisin and N-acetylneuraminic acid aldolase for the synthesis of a fluorescent sialic acid," J Org Chem. 59(26):8279-80 (1994).

Fleischer, "Mechanism of glycosylation in the Golgi apparatus," J Histochem Cytochem. 31 (8):1033-40 (1983).

Forno et al., "N- and O-linked carbohydrates and glycosylation site occupancy in combinant human granulocyte-macrophage colony-stimulating factor secreted by a Chinese hamster ovary cell line," Eur J Biochem. 271 (5):907-19 (2004).

Forrer et al., "Chip-based gel electrophoresis method for the quanitification of half-antibody species in laG4 and their by- and degradation products," Anal Biochem. 334:81-8 (2004).

Fukuda et al., "Survival of recombinant erythropoietin in the circulation: the role of carbohydrates", Blood. 73(1):84-89 (1989).

Gajdos et al., "Intravenous Immunoglobulin for myasthenia gravis," Cochrane Database of Systematic Reviews, 2012, 12:1-30.

Gates et al., "Glycobiology Analysis Manual," <http://www.sigmaaldrich.com/lifescience/proteomics/post-translational-analysis/glycosylation/glycoprotein-analysis-manual.html>. retrieved on Nov. 23, 2016 (132 pages).

Gawlitzek et al., "Ammonium alters N-glycan structures of recombinant TNFR-lgG: degradative versus biosynthetic mechanisms", Biotechnol Bioeng. 68(6):637-46 (2000).

Gawlitzek et al., "Characterization of changes in the glycosylation pattern of recombinant proteins from BHK-21 cells due to different culture conditions", J Biotechnol. 42(2):117-131 (1995).

Gilar et al., "Characterization of glycoprotein digests with hydrophilic interaction chromatography and mass spectrometry." Anal Biochem. 417(1 ):80-8 (2011 ).

Goetze et al., "High-mannose glycans on the Fe region of therapeutic lgG antibodies increase serum clearance in humans," Glvcobioloqy. 21 (7):949-59 (2011 ).

Goldman et al., "Monitoring recombinant human interferon-gamma N-glycosylation during perfused fluidized-bed and stirred-tank batch culture of CHO cells", Biotechnol Bioeng. 60(5):596-607 (1998).

Greer, "Biosimilar developers face a reference-product dilemma," <http://license.icopyright.net/user/viewFreeUse.act?fuid=MTYwMTgONDk%3D>, retrieved on Apr. 9, 2012 (3 pages).

Griciuc et al., "Alzheimer's Disease Risk Gene CD33 Inhibits Microglial Uptake of Amyloid Beta," Neuron., 2013, 78:631-643.

Gu et al., "Improvement of interferon-gamma sialylation in Chinese hamster ovary cell culture by feeding of N-acetylmannosamine", Biotechnol Bioeng. 58(6):642-48 (1998).

Guhr et al., "Enrichment of Sialylated IgG by Lectin Fractionation Does Not Enhance the Efficacy of Immunoglobulin G in a Murine Model of Immune Thrombocytopenia," PLOS One., Jun. 2011, 6(6):e21246.

Hahn et al., "Intravenous immunoglobulin treatment in chronic inflammatory demyelinating polyneuropathy: A double-blind, placebo-controlled, cross-over study," Brain, Aug. 1996, 119:1067-1077.

Hallewell et al., "Genetically Engineered Polymers of Human CuZn Superoxide Dismutase Biochemistry and Serum Half-lives," J Biol Chem., 1989, 264:5260-5268.

Hara et al., "Determination of mono-O-acetylated N-acetylneuraminic acids in human and rat sera by fluorometric high-performance liquid chromatography," Anal Biochem. 179(1):162-6 (1989).

Hara et al., "Determination of mono-O-acetylated N-acetylneuraminic acids in human and rat sera by fluorometric high-performance liquid chromatography," Anal Biochem., 1989, 179(1):162-166.

Harn et al., "Biophysical Signatures of Monoclonal Antibodies," Current Trends in Monoclonal Antibody Development and Manufacturing, 2010, 229-246 (Abstract Only).

Hendrick et al., "Increased productivity of recombinant tissular plasminogen activator (t-PA) by butyrate and shift of temperature: a cell cycle phases analysis", Cytotechnology. 36(1-3):71-83 (2001).

Hewitt et al., "Solution and solid-support synthesis of a potential leishmaniasis carbohydrate vaccine", J Org Chem. 66(12):4233-43 (2001).

Hickman et al., "Microglial dysfunction and defective beta-amyloid clearance pathways in aging Alzheimer's disease mice," J Neuroscience., 2008, 28(33):8354-8360.

Hills et al., "Metabolic control of recombinant monoclonal antibody N-glycosylation in GS-NS0 cells," Biotechnol Bioeng. 75(2):239-51 (2001).

Hincal, "An introduction to safety issues in biosimilars/follow-on biopharmaceuticals," J Med CBR Def. 7 (2009) (18 pages).

Hirabayashi et al., "Separation technologies for glycomics", J Chromatog B Analyst Technol Biomed Life Sci. 771 (1-2):67-87 (2002) (Abstract Only) (2 pages).

Hoja-Lukowicz et al., "High-mannose-type oligosaccharides from human placental arylsulfatase A are core fucosylated as confirmed by MALDI MS", Glycobiology. 10(6):551-7(2000).

Hokke et al., "Sialylated carbohydrate chains of recombinant human glycoproteins expressed in Chinese hamster ovary cells contain traces of N-glycolylneuraminic acid," FEBS Lett. 275(1-2):9-14 (1990).

Hosoi et al., "Modulation of oligosaccharide structure of a pro-urokinase derivative (pro-UK delta GS1) by changing culture conditions of a lymphoblastoid cell line Namalwa KJM-1 adapted to serum-free medium," Cytotechnology. 19(2):125-35 (1996).

Hossler et al., "Systems analysis of N-glycan processing in mammalian cells," PLoS One. 2(8):e713 (2007) (17 pages).

Houde et al., "Characterization of IgG1 Conformation and Conformational Dynamics by Hydrogen/Deuterium Exchange Mass Spectrometry," Anal. Chem., 2009, 81:2644-2651.

Huang et al., "Chemoenzymatic Glycoengineering of intact IgG Antibodies for Gain of Functions," Journal of the American Chemical Society, Jul. 16, 2012, 134(29):12308-12318.

Imai-Nishiya et al., "Double knockdown of alpha1 ,6-fucosyltransferase (FUT8) and GDPmannose 4,6-dehydratase (GMO) in antibody-producing cells: a new strategy for generating fully non-fucosylated therapeutic antibodies with enhanced ADCC", BMC Biotechnol. 7:84 (2007) (13 pages).

Inouye & Inouye, "Up-promoter mutations in the lpp gene of Escherichia coli," Nucleic Acids Res., 1985, 13:3101-3109.

International Preliminary Report on Patentability for International Application No. PCT/US2019/055983, dated Apr. 22, 2021, 13 pages.

International Preliminary Report on Patentability for International Application No. PCT/US2013/052040, mailed Jun. 18, 2015 (13 pages).

International Preliminary Report on Patentability for International Application No. PCT/US2014/036413, dated Nov. 3, 2015 (25 pages).

International Preliminary Report on Patentability for International Application No. PCT/US2014/060363, issued Apr. 19, 2016 (6 pages).

International Preliminary Report on Patentability for International Parent Application No. PCT/US2014/037761, dated Nov. 17, 2015 (8 pages).

International Search Report and Written Opinion for International Application No. PCT/US13/52040, mailed Dec. 3, 2013 (23 pages).

(56)　　　References Cited

OTHER PUBLICATIONS

International Search Report and Written Opinion for International Application No. PCT/US14/36413, mailed Nov. 21, 2014 (42 pages).
International Search Report and Written Opinion for International Application No. PCT/US14/60363, mailed February 4, 2015 (14 pages).
International Search Report and Written Opinion for International Application No. PCT/US2014/037761, mailed Oct. 10, 2014 (17 pages).
International Search Report and Written Opinion for International Patent Application No. PCT/US2013/043786, mailed Jul. 3, 2014 (21 pages).
International Search Report and Written Opinion in International Application No. PCT/US2019/055983, dated Jan. 10, 2020, 16 pages.
International Search Report and Written Opinion in International Application No. PCT/US2019/055987, dated Feburary 20, 2020, 14 pages.
Jabs et al., "Fast and Extensive Mass Spectrometry Characterization of Theraputic mAbs: The Panitumumab Case Study," CASSS Mass Spec Meeting, Poster 125 (2012) (1 page).
Jain et al., "Alpha4beta1 integrin mediates the recruitment of immature dendritic cells across the blood-brain barrier during experimental autoimmune encephalomyelitis," J Immunol., 2010, 184(12):7196-7206.
Janke and Jong., "Impact of IVIg on the interaction between activated T cells and microglia," Neural Res., 2006, 28:270-274.
Jefferis et al., "IgG-Fc-mediated effector functions: molecular definition of interaction sites for effector ligands and the role of glycosylation," Immunol. Rev., 1998, 163:59-76.
Jefferis, "Glycosylation as a strategy to improve antibody-based therapeutics," Nature Reviews, 2009, 8:226-234.
Johnson et al., "Cation exchange-HPLC and mass spectrometry reveal C-terminal amidation of an IgG1 heavy chain," Anal. Biochem., 2007, 360:75-83.
Joosten et al., "Effect of culture conditions on the degree of sialylation of a recombinant glycoprotein expressed in insect cells", Biotechnol Proq. 19(3):739-49 (2003).
Joziasse et al., "Branch specificity of bovine colostrum CMP-sialic acid: Gal beta 1-4GlcNAc-R alpha 2-6-sialyltransferase. Sialylation of bi-, tri-, and tetraantennary oligosaccharides and qlycopeptides of the N-acetyllactosamine type," J Biol Chem. 262(5):2025-33 (1987).
Kakehi et al., "Analysis of glycoproteins, glycopeptides and glycoprotein-derived oligosaccharides by high-performance capillary electrophoresis," J Chromatogr. 720(1-2):377-93 (1996).
Kalodiki et al., "New and generic anticoagulants and biosimilars: safety considerations," Clin Appl Thromb Hemost. 17(2):136-9 (2011) (5 pages).
Kanda et al., "Comparison of biological activity among nonfucosylated therapeutic IgG1 antibodies with three different N-linked Fe oligosaccharides: the high-mannose, hybrid, and complex types," Glycobiology. 17(1):104-18 (2006).
Kanda et al., "Establishment of a GDP-mannose 4,6-dehydratase (GMO) knockout host cell line: A new strategy for generating completely non-fucosylated recombinant therapeutics," Journal of Biotechnol. 130(3):300-10 (2007) (Abstract Only).
Kaneko et al., "Anti-inflammatory activity of immunoglobulin G resulting from Fe sialylation." Science. 313(5787):670-3 (2006).
Kaneko et al., "Pathology and protection in nephrotoxic nephritis is determined by selective engagement of specific Fe receptors." J Exp Med. 203(3):789-97 (2006).
Kasermann et al., "Analysis and Functional Consequences of Increased Fab-Sialylation of Intravenous Immunoglobulin (IVIG) after Lectin Fractionation," PLOS One, Jun. 2012, 7(6):e37243 (With Supplemental Material).
Kawashima et al., "Tyrosine kinase activity of epidermal growth factor receptor is regulated by GM3 binding through carbohydrate to carbohydrate interactions," J Biol Chem. 284(10):6147-55 (2009).

Keiser et al., "Direct isolation and sequencing of specific protein-binding glycosaminoglycans," Nat Med. 7(1):123-8 (2001).
Keppler et al., "Biosynthetic modulation of sialic acid-dependent virus-receptor interactions of two primate polyoma viruses," J Biol Chem. 270(3):1308-14 (1995).
Kile et al., "IVIG treatment of mild cognitive impairment due to Alzheimer's disease: a randomised double-blinded exploratory study of the effect on brain atrophy, cognition and conversion to dementia," J Neurol Neurosurg Psychiatry, Sep. 2015, 0: 1-7.
Kim et al., "Production and N-glycan analysis of secreted human erythropoietin glycoprotein in stably transfected Drosophila S2 cells, " Biotechnol Bioeng. 92(4):452-61 (2005).
Kosa et al., "Modification of cell surfaces by enzymatic introduction of special sialic acid analogues," Biochem Biophys Res Commun. 190(3):914-20 (1993).
Krapp et al., "Structural analysis of human IgG-Fc glycoforms reveals a correlation between glycosylation and structural integrity," J Mol Biol. 325(5):979-89 (2003).
Kunkel et al., "Comparisons of the glycosylation of a monoclonal antibody produced under nominally identical cell culture conditions in two different bioreactors," Biotechnol Prog. 16(3):462-70 (2000).
Kunkel et al., "Dissolved oxygen concentration in serum-free continuous culture affects N-linked glycosylation of a monoclonal antibody," J Biotechnol. 62(1):55-71 (1998).
Kuter et al., "Thrombopoietin and platelet production in chronic immune thrombocytopenia," Hematol Oncol Clin North Am., Dec. 2009, 23(6):1193-1211.
Kuwano et al., Successful Treatment of Dermatomyositis with High-dose Intravenous Immunoglobulin, Acta Dermato-Venereologica, 2006, 86(2):158-159.
Lance et al., "Isolation and characterization of a partial cDNA for a human sialyltransferase." Biochem Biophys Res Commun. 164(1):225-32 (1989).
Lapointe et al., "IVIg therapy in brain inflammation: etiology-dependent differential effects on leucocyte recruitment," Brain, 2004, 127(Pt 12):2649-2656.
Lattova et al., "Alterations in glycopeptides associated with herceptin treatment of human breast carcinoma MCF-7 and T-lymphoblastoid cells," Mol Cell Proteomics. 10(9):M111.007765 (2011) (11 pages).
Le Floch et al., "HPCE monitoring of the N-glycosylation pattern and sialylation of murine erythropoietin produced by CHO cells in batch processes," Biotechnol Prog. 20(3):864-71 (2004).
Legaigneur, et al., "Exploring the acceptor substrate recognition of the human beta-Galactoside alpha2,6-Sialytransferase," J. Biol. Chem., 2001, 276:21608-617.
Lifely et al., "Glycosylation and biological activity of CAMPATH-1 H expressed in different cell lines and grown under different culture conditions," Glycobiology. 5(8):813-22 (1995).
Lin et al., "Unusual stereoselectivity in sialic acid aldolase-catalyzed aldol condensations: synthesis of both enantiomers of high-carbon monosaccharides," J Am Chem Soc. 114(26):10138-45 (1992).
Lipscomb et al., "Effect of production method and gene amplification on the glycosylation pattern of a secreted reporter protein in CHO cells," Biotechnol Prog. 21 (1):40-9 (2005).
Live et al., "Conformational influences of glycosylation of a peptide: a possible model for the effect of glycosylation on the rate of protein folding," Proc Natl Acad Sci USA. 93(23):12759-61 (1996).
Logan & Shenk, "Adenovirus tripartite leader sequence enhances translation of mRNAs late after infection," Proc Natl Acad Sci USA., 1984, 81:355-359.
Lopez-Avalos et al., "The UDPase activity of the Kluyveromyces lactis Golgi GDPase has a role in uridine nucleotide sugar transport into Golgi vesicles," Glycobiology. 11(5):413-22 (2001).
Ma, et al., "Two naturally occuring alpha2,6-Sialytransferase forms with a single amino acid change in the catalytic domain differ in their catalytic activity and proteolytic processing," J. Biol. Chem., 1997, 272:672-279.
MacMillan et al., "Selective in vitro glycosylation of recombinant proteins: semi-synthesis of novel homogeneous glycoforms of human erythropoietin," Chem Biol. 8(2):133-45 (2001).

(56) References Cited

OTHER PUBLICATIONS

Mattu et al., "The Glycosylation and Structure of Human Serum IgA1, Fab, and Fc Regions and the Role of N-Glycosylation on FcαO Receptor Interactions," J. Biol. Chem., 1998, 273:2260-2272.

Miller et al., "Characterization of site-specific glycation during process development of a human therapeutic monoclonal antibody," J Pharm Sci. 100(7):2543-50 (2011).

Misra, "Are biosimilars really generics?" Expert Opin Biol Ther. 10(4):489-94 (2010).

Moran et al., "A systematic approach to the validation of process control parameters for monoclonal antibody production in fed-batch culture of a murine myeloma," Biotechnol Bioeng. 69(3):242-55 (2000).

Morrison, "Transfectomas provide novel chimeric antibodies," Science, 1985, 229(4719):1202-1207.

Mueller et al., "Recombinant glycoprotein product quality in proliferation-controlled BHK-21 cells, " Biotechnol Bioeng. 65(5):529-36 (1999).

Naert et al., "CC chemokine receptor 2 deficiency aggravates cognitive impairments and amyloid pathology in a transgenic mouse model of Alzheimer's disease," J Neuroscience., 2011, 31(16):6208-6220.

Nairn et al., "Regulation of glycan structures in animal tissues: transcript profiling of glycanrelated genes," J Biol Chem. 283(25):17298-313 (2008).

Nam et al., "The effects of culture conditions on the glycosylation of secreted human placental alkaline phosphatase produced in Chinese hamster ovary cells," Biotechnol Bioeng. 100(6):1178-92 (2008).

Nettleton et al., "Role of Glycosylation Sites in the IgE Fc Molecule," Int. Arch. Allergy Immunol., 1995, 107:328-329.

Nimmerjahn et al., "The antiinflammatory activity of IgG: the intravenous IgG paradox," J Exp Med. 204(1 ):11-5 (2007).

Nowicki, "Basic facts about biosimilars," Kidney Blood Press Res. 30:267-72 (2007).

Nyberg et al., "Metabolic effects on recombinant interferon-gamma glycosylation in continuous culture of Chinese hamster ovary cells," Biotechnol Bioeng. 62(3):336-47 (1999).

Oh et al., "Effect of N-acetylcystein on butyrate-treated Chinese hamster ovary cells to improve the production of recombinant human interferon-beta-1 a," Biotechnol Prog. 21 (4):1154-64 (2005).

Pace et al., "Characterization of minor N-linked glycans on antibodies using endo H release and MALDI-mass spectrometry," Anal Lett. 42:1711-24 (2009).

Park et al., "Expression of carbamoyl phosphate synthetase I and ornithine transcarbamoylase genes in Chinese hamster ovary dhfr-cells decreases accumulation of ammonium ion in culture media," J Biotechnol. 81 (2-3):129-40 (2000).

Parmley, Sweetenina Immunoalobulins. Biocenturv Innovations. Bernstein (2015)(2 paaes).

Pekar and Sukumar, "Quantitation of aggregates in therapeutic proteins using sedimentation velocity analytical ultracentrifugation: practical considerations that affect precision and accuracy," Anal. Biochem., 2007, 367:225-237.

Plante et al., "Automated solid-phase synthesis of oligosaccharides," Science. 291 (5508):1523-7 (2001).

Plante et al., "Formation of beta-glucosamine and beta-mannose linkages using glycosyl phosphates," Org Lett. 2(24):3841-3 (2000).

Puli et al., "Effects of human intravenous immunoglobulin on amyloid pathology and neuroinflammation in a mouse model of Alzheimer's disease," J Neuroinflammation., 2012, 9:105.

Rader, "Nomenclature of new biosimilars will be highly controversial," BioProcess International. 9:28-32 (2011).

Raju, "Terminal sugars of Fe glycans influence antibody effector functions of IgGs," Curr Opin Immunol. 20(4):471-8 (2008).

Ramakrishna et al., Passively Administered Pooled Human Immunoglobulins Exert IL-10 Dependent Anti-Inflammatory Effects that Protect against Fatal HSV Encephalitis., Jun. 2, 2011, 7(6):1-17.

Raymond et al., "Production of Highly Sialylated Monoclonal Antibodies," Biochemistry, Genetics and Molecular Bioloqv-Glvcosvlation. Stefana Petrescu, 397-418 (2012).

Reitman et al., "Mouse lymphoma cell lines resistant to pea lectin are defective in fucose metabolism", J Biol Chem. 255(20):9900-6 (1980).

Restelli et al., "The effect of dissolved oxygen on the production and the glycosylation profile of recombinant human erythropoietin produced from CHO cells", Biotechnol Bioeng. 94(3):481-94 (2006).

Ripka et al., "Two Chinese hamster ovary glycosylation mutants affected in the conversion of GDP-mannose to GDP-fucose," Arch Biochem Biophys. 249(2):533-45 (1986).

Ritzenthaler et al., "Reevaluation of the effects of brefeldin A on plant cells using tobacco Bright Yellow 2 cells expressing Golgi-targeted green fluorescent protein and COPI antisera, " Plant Cell. 14(1):237-61 (2002).

Robinson et al., "Characterization of a recombinant antibody produced in the course of a high yield fed batch process," Biotechnol Bioeng. 44(6):727-35 (1994).

Rodriguez et al., "Enhanced production of monomeric interferon-beta by CHO cells through the control of culture conditions," Biotechnol Prog. 21(1):22-30 (2005).

Roger, "Biosimilars: current status and future directions," Expert Opin Biol Ther. 10(7):1011-8 (2010).

Rudiger et al., "Breaking the sugar code: six levels of affinity regulation in glycan-lectin interaction," Crackina the Suaar Code by Naviaatina the Glycospace. Germany, 11-28 (2011 ).

Ruisi et al., "Stability of measurement of the immature platelet fraction," Am J Hematol. 85(8):622-4 (2010).

Ruther et al., "Easy identification of cDNA clones," EMBO, 1983, 12:1791-1794.

Santell et al., "Aberrant metabolic sialylation of recombinant proteins expressed in Chinese hamster ovary cells in high productivity cultures," Biochem Biophys Res Commun. 258(1):132-7 (1999).

Sasaki et al., "Site-specific glycosylation of human recombinant erythropoietin: analysis of glycopeptides or peptides at each glycosylation site by fast atom bombardment mass spectrometry," Biochemistry. 27(23):8618-26 (1988).

Sazinsky et al., "Aglycosylated immunoglobulin G1 variants productively engage activating Fc receptors," Proc Natl Acad Sci USA., Dec. 23, 2008, 105(51):20167-20172.

Schellekens and Moore, "Clinical comparability and European biosimilar regulations," Nat Biotechnol, Jan. 2010, 28(1):28-31.

Schellekens, "Biosimilar therapeutics—what do we need to consider?" NDT Plus, 2009, 2(Suppl_ 1):i27-i36.

Schiestl et al., "Acceptable changes in quality attributes of glycosylated biopharmaceuticals." Nat Biotechnol. 29(4):310-2 (2011).

Schulz et al., "Mediators of galactose sensitivity in UDP-galactose 4'-epimerase-impaired mammalian cells," J Biol Chem. 280(14):13493-502 (2005).

Schuster et al., "Improved effector functions of a therapeutic monoclonal Lewis Y-specific antibody by glycoform engineering," Cancer Res. 65(17):7934-41 (2005).

Schwab et al., "Intravenous immunoglobulin therapy: how does IgG modulate the immune system?," Nat Rev Immunol. 13(3): 176-89 (2013).

Schwab et al., "IVI g-mediated amelioration of ITP in mice is dependent on sialic acid and SIGNR 1," Eur J Immunol., Jan. 26, 2012, 42:826-830.

Segal et al., "Introduction: bispecific antibodies," J Immunol Methods., 2001, 248:1-6.

Sekhon et al., "Biosimilars: an overview," Biosimilars. 2011 (1 ):1-11 (2011).

Senger et al., "Effect of shear stress on intrinsic CHO culture state and glycosylation of recombinant tissue-type plasminogen activator protein," Biotechnol Prog. 19(4):1199-209 (2003).

Serrato et al., "Heterogeneous conditions in dissolved oxygen affect N-glycosylation but not productivity of a monoclonal antibody in hybridoma cultures", Biotechnol Bioeng. 88(2):176-188 (2004).

Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology. 1(2):187-191 (1991).

(56)    References Cited

OTHER PUBLICATIONS

Shang et al., "Development and application of a robust N-glycan profiling method for heightened characterization of monoclonal antibodies and related glycoproteins," J Ph arm Sci. 103(7): 1967-78 (2014).

Sherman, Rachel E., "Biosimilar Biological Products". Biosimilar Guidance Webinar. Food and Drug Administration (2012) (22 pages).

Shinkawa et al., "The absence of fucose but not the presence of galactose or bisecting Nacetylglucosamine of human lgG1 complex-type oligosaccharides shows the critical role of enhancing antibody-dependent cellular cytotoxicity," J Biol Chem. 278(5):3466-73 (2003).

Siberil et al., "Intravenous immunoglobulins in autoimmune and inflammatory diseases: a mechanistic perspective." Ann NY Acad Sci. 1110:497-506 (2007).

Sokolowski et al., "Conformational analysis of biantennary glycans and molecular modeling of their complexes with lentil lectin", J Mal Graph Model. 15(1):37-42 (1997).

Sparks et al., "Synthesis of potential inhibitors of hemagglutination by Influenza virus: chemoenzymic preparation of N-5 analogs of N-acetylneuraminic acid", Tetrahedron. 49(1):1-12 (1993).

Spearman et al., "Production and glycosylation of recombinant beta-interferon in suspension and cytopore microcarrier cultures of CHO cells", Biotechnol Prog. 21 (1):31-9 (2005).

Srinivas et al., "Assessment of dose proportionality, absolute bioavailability, and immunogenicity response of CTLA4lg (BMS-188667), a novel immunosuppressive agent, following subcutaneous and intravenous administration to rats," Pharm Res. 14(7) :911-6 (1997).

Srinivas et al., "Pharmacokinetics and pharmacodynamics of CTLA4lg (BMS-188667), a novel immunosuooressive agent, in monkeys following multiple doses," J Pharm Sci. 85(1):1-4 (1996).

Stadlmann et al., "A close look at human IgG sialylation and subclass distribution after lectin fractionation," Proteomics, 2009, 9:4143-4153.

Stadlmann et al., "Analysis of immunoglobulin glycosylation by LC-ES I-MS of glycopeptides and oligosaccharides," Proteomics. 8:2858-71 (2008).

Stadlmann et al., "Analytical and Functional Aspects of Antibody Sialylation," J Clin Immunol., May 2010, 30(Suppl 1):S15-S19.

Sticher, et al., "Purification and characterization of alpha(2-6)-sialyltransferase from human liver," Blycoconjugate J., 1991, 8:45-54.

Sung et al., "Effect of sodium butyrate on the production, heterogeneity and biological activity of human thrombopoietin by recombinant Chinese hamster ovary cells," J Biotechnol. 112(3):323-35 (2004).

Takashima, "Characterization of Mouse Sialyltransferase Genes: Their Evolution and Diversity," Biosci. Biotech. & Biochem., 2008, 72(5):1155-1167.

Takeuchi et al., "Structures and functional roles of the sugar chains of human erythropoietins," Glycobiology. 1(4):337-346 (1991).

Tan et al., "Characterization and comparison of commercially available TNF receptor 2-Fc fusion protein products." Mabs. 4(6):761-74 (2012).

Third-Party Observation pursuant to Rule 114(2) EPC for European Patent Application No. 13796989.5, dated Jun. 22, 2016 (14 pages).

Townsend, "Chapter 5 Analysis of Glycoconjugates Using High-pH Anion-Exchange Chromatography," Journal of Chromatography Library, 1995, 58:181-209.

Tran et al., "Separation of carbohydrate-mediated microheterogeneity of recombinant human erythropoietin by free solution capillary electrophoresis. Effects of pH, buffer type and organic additives," J Chromatogr. 542(2):459-71 (1991).

Trombetta et al., "Glycoprotein reglucosylation and nucleotide sugar utilization in the secretory pathway: identification of a nucleoside diphosphatase in the endoplasmic reticulum," EMBO J. 18(12):3282-92 (1999).

Trummer et al., "Process parameter shifting: Part I. Effect of DOT, pH, and temperature on the performance of Epo-Fc expressing CHO cells cultivated in controlled batch bioreactors," Biotechnol Bioeng. 94(6):1033-44 (2006).

Tutt et al., "Trispecific F(ab')3 derivatives that use cooperative signaling via the TCR/CD3 complex and CD2 to activate and redirect resting cytotoxic T cells," J lmmunol., 1991, 147:60-69 (Abstract Only).

Umana et al., "Engineered glycoforms of an antineuroblastoma lgG1 with optimized antibodydependent cellular cytotoxic activity," Nat Biotechnol. 17(2):176-80 (1999).

Van Berkel et al., "N-linked glycosylation is an important parameter for optimal selection of cell lines producing biopharmaceutical human lgG," Biotechnol Prag. 25(1):244-51 (2009).

Van Den Nieuwenhof et al., "Recombinant glycodelin carrying the same type of glycan structures as contraceptive glycodelin-A can be produced in human kidney 293 cells but not in Chinese hamster ovary cells," Eur J Biochem. 267(15):4753-62 (2000).

Van Heeke & Schuster, "Expression of Human Asparagine Synthetase in Escherichia coli," J Biol Chem., 1989, 24:5503-5509.

Varki, "Radioactive tracer techniques in the sequencing of glycoprotein oligosaccharides," FASEB J. 5(2):226-35 (1991).

Venkataraman et al., "Sequencing complex polysaccharides," Science. 286(5439):537-42 (1999).

Von Der Lieth, "Expanding proteomics to glycobiology: biocomputing approaches understanding the function of sugar," Pacific Symposium on Biocomputing; Kauai, Hawaii (Abstract only) (2 pages) (2002).

Wang et al., "Characterization and comparison of disulfide linkages and scrambling patterns in therapeutic monoclonal antibodies: using LC-MS with electron transfer dissociation," Anal Chem. 83:3133-40 (2011).

Wang et al., "EDEM an ER quality control receptor," Nat Struct Biol. 10(5):319-21 (2003).

Ward et al., "Binding activities of a repertoire of single immunoglobulin variable domains secreted from Escherichia coli," Nature, 1989, 341:544-546.

Warrington et al., in Naturally Occurring Antibodies (NAbs), edited by Hans U. Lutz, copyright 2012 Landes Bioscience and Springer Science+Business Media.

Washburn et al., "Controlled tetra-Fe sialylation of IVlg results in a drug candidate with consistent enhanced anti-inflammatory activity," Proc Natl Acad Sci U.S.A. 112(11):E1297-306 (2015).

Watson et al., "Capillary electrophoretic separation of human recombinant erythropoietin (r-HuEPO) glycoforms," Anal Biochem. 210(2):389-93 (1993).

Watson et al., "Structure determination of the intact major sialylated oligosaccharide chains of recombinant human erythropoietin expressed in Chinese hamster ovary cells," Glycobiology. 4(2):227-37 (1994).

Webb et al., "Structural characterization of intact, branched oligosaccharides by high performance liquid chromatography and liquid secondary ion mass spectrometry," Anal Biochem. 169(2):337-49 (1988).

Weikert et al., "Engineering Chinese hamster ovary cells to maximize sialic acid content of recombinant glycoproteins," Nature Biotechnology, Nov. 1999, 17:1116-1121.

Weiner et al., "A sensitive enzyme immunoassay for the quantitation of human CTLA4lg fusion protein in mouse serum: pharmacokinetic application to optimizing cell line selection," J Pharm Biomed Anal. 15(5):571-9 (1997).

Weinstein et al., "Primary structure of beta-galactoside alpha 2,6-sialyltransferase. Conversion of membrane-bound enzyme to soluble forms by cleavage of the NH2-terminal signal anchor," J Biol Chem., 1987, 262:17735-17743.

Widiapradja et al., "Intravenous immunoglobulin protects neurons against amyloid beta-peptide toxicity and ischemic stroke by attenuating multiple cell death pathways," J Neurochem., 2012, 122:321-332.

Wilson et al., "The structure of an antigenic determinant in a protein," Cell, 1984, 37(3):767-778 (Abstract Only).

Wong et al., "Impact of dynamic online fed-batch strategies on metabolism, productivity and Nglycosylation quality in CHO cell cultures," Biotechnol Bioeng. 89(2):164-77 (2005).

(56) References Cited

OTHER PUBLICATIONS

Wootla et al., "Polyclonal and monoclonal antibodies in clinic," Methods Mol Biol., Sep. 2013, (1060):79-110.

Wopereis et al., "Mechanisms in protein O-glycan biosynthesis and clinical and molecular aspects of protein O-glycan biosynthesis defects: a review," Clin Chem. 52(4):574-600 (2006).

Wormold et al., "Variations in oligosaccharide-protein interactions in immunoglobulin G determine the site-specific glycosylation profiles and modulate the dynamic motion of the Fc oligosaccharides," Biochemistry, 1997, 36(6):1370-1380.

Wright et al., "Effect of glycosylation on antibody function: implications for genetic engineering," Trends Biotech, 1997, 15:26-32.

Wright et al., "In vivo trafficking and catabolismof IgG1 antibodies with Fc associated carbohydrates of differing structure," Glycobiology. 10(12):1347-55 (2000).

Wuhrer et al., "Glycoproteomics based on tandem mass spectrometry of glycopeptides," J. Chromatogr. B., 2007, 849:115-128.

Xie et al., "Rapid comparison of a candidate biosimilar to an innovator monoclonal antibody with advanced liquid chromatography and mass spectrometry technologies," MAbs. 2(4):379-94 (2010).

Yan et al., "Analysis of post-translational modifications in recombinant monoclonal antibody IgG1 by reversed-phase liquid chromatography/mass spectrometry," J Chromatogr A. 1164(1-2):153-61 (2007).

Yang et al., "Achievement of high cell density and high antibody productivity by a controlled-fed perfusion bioreactor process," Biotechnol Bioeng. 69(1):74-82 (2000).

Yang et al., "Bio-basis function neural network for prediction of protease cleavage sites in proteins," IEEE Trans Neural Netw. 16(1):263-74 (2005).

Yang et al., "Effect of ammonia on the glycosylation of human recombinant erythropoietin in culture," Biotechnol Prog. 16(5):751-9 (2000).

Ye et al., "N-glycan branching requirement in neuronal and postnatal viability," Glycobiology. 14(6):547-58 (2004).

Yoon et al., "Effect of culture pH on erythropoietin production by Chinese hamster ovary cells grown in suspension at 32.5 and 37.0 degrees C.," Biotechnol Bioeng. 89(3):345-56 (2005).

Yoon et al., "Effect of simultaneous application of stressful culture conditions on specific productivity and heterogeneity of erythropoietin in Chinese hamster ovary cells," Biotechnol Prog. 20(4):1293-6 (2004).

Yuen et al., "Relationships between the N-glycan structures and biological activities of recombinant human erythropoietins produced using different culture conditions and purification procedures," Br J Haematol. 121 (3):511-26 (2003).

Yuk et al., "Changes in the overall extent of protein glycosylation by Chinese hamster ovary cells over the course of batch culture", Biotechnol Appl Biochem. 36(Pt 2):133-40 (2002).

Yuk et al., "Glycosylation by Chinese hamster ovary cells in dolichol phosphate-supplemented cultures," Biotechnol Appl Biochem. 36(Pt 2):141-7 (2002).

Zhang et al. "Sialylated intravenous immunoglobulin suppress anti-ganglioside antibody mediated nerve injury," Exp Neurol., May 18, 2016, 282:49-55.

Zhang et al., "Glycoengineered Pichia produced anti-HER2 is comparable to trastuzumab in preclinical study." MAbs. 3(3):289-98 (2011).

Zhang et al., "Quantitative analysis and process monitoring of site-specific glycosylation microheterogeneity in recombinant human interferon-gamma from Chinese hamster ovary cell culture by hydrophilic interaction chromatography," J Chromatogr B Bio med Sci Appl. 712(1-2):73-82 (1998).

U.S. Appl. No. 18/218,535, filed Jul. 5, 2023.

Alistair Rogers and Yves Gibon, "Enzyme Kinetics: Theory and Practice," Plant Metabolic Networks, 2009, Chapter 4, pp. 71-103.

Altschul, S. F., Gish, W., Miller, W., Myers, E. W., & Lipman, D. J. (1990). Basic local alignment search tool. Journal of Molecular Biology, 215(3), 403-410.

Arnold et al., "The impact of glycosylation on the biological function and structure of human immunoglobulins," Annu Rev Immunol., 2007, 25:21-50.

Arroyo et al., "Hyper-Sialylated IgG M254, an Innovative Therapeutic Candidate, Evaluated in Healthy Volunteers and in Patients with Immune Thrombocytopenia Purpura: Safety, Tolerability, Pharmacokinetics, and Pharmacodynamics," Blood, 2019, 134(Supplement 1):1090.

Baxter International Inc. (Jun. 25, 2012). Baxter announces FDA approval for GAMMAGARD Liquid as a treatment for multifocal motor neuropathy. Retrieved from https://investor.baxter.com/investors/events-and-news/news/press-release-details/2012/Baxter-Announces-FDA-Approval-for-GAMMAGARD-LIQUID-as-a-Treatment-for-Multifocal-Motor-Neuropathy/default.aspx.

Beneduce et al., "Anti-inflammatory Activity of IgG-Fc," Curr Top Microbiol Immunol., 2019;423:35-62.

Benesova et al., "Affinity Interactions as a Tool for Protein Immobilization," In: Magdeldin S, editor. Affinity Chromatography: InTech. 2012;29-46.

Berry M. J. et al. Substitution of cysteine for selenocysteine in type I iodothyronine deiodinase reduces the catalytic efficiency of the protein but enhances its translation, Endocrinology, 1992, v. 131, No. 4, pp. 1848-1852, p. 1848.

Bril et al., "IGIV in Neurology—Evidence and Recommendations," Can J Neurol Sci., 1999, 26:139-152.

Broun et al., "Catalytic Plasticity of Fatty Acid Modification Enzymes Underlying Chemical Diversity of Plant Lipids", Science, 1998, v. 282, p. 1315-1317 (see abstract).

Brown et al., "Deoxygenated disaccharide analogs as specific inhibitors of beta 1,4-galactosyltransferase 1 and selectin-mediated turmor metastasis." J. Biol. Chem. 284:4952-4959 (2009).

Burckhardt et al., "Immunoglobulin G subclass distribution in three human intravenous immunoglobulin preparations," Vox Sang., 1989, 57(1):10-14.

Cai et al., "Ensuring the Biological Safety of Plasma-Derived Therapeutic Proteins: Detection, Inactivation, and Removal of Pathogens," BioDrugs 19(2):79-96 (2005).

CAS No. 9003-11-6, Block copolymer of ethylene oxide and propylene oxide, Sigma-Aldrich, retrieved on Dec. 14, 2022, retrieved from URL <https://www.products.pcc.eu/en/cas-numbers/9003-11-6/?list type=list>, 6 pages.

Cats et al., "Correlates of outcome and response to IVIg in 88 patients with multifocal motor neuropathy," Neurology, Aug. 31, 2010, 75(9):818-825.

Chen, Rui et al. "Glycoproteomics analysis of human liver tissue by combination of multiple enzyme digestion and hydrazide chemistry." Journal of proteome research vol. 8,2 (2009):651-61. doi:10.1021/pr8008012.

Chintalacharuvu et al., "Treatment of Collagen Induced Arthritis by Proteolytic Enzymes: Immunomodulatory and Disease Modifying Effects," J Rheumatology., Sep. 2001, 28(9):2049-2059.

Cho, Hee Jun et al: "Efficient Interleukin-21 Production by Optimization of Codon and Signal Peptide in Chinese Hamster Ovarian Cells", Journal of Microbiology and Biotechnology, vol. 29, No. 2, Feb. 28, 2019 (Feb. 28, 2019), pp. 304-310, XP055644468, Korea ISSN: 1017-7825, DOI: 10.4014/jmb.1811.11042.

Clark-Curtiss, J. E., & Curtiss, R. III. (1983). Analysis of recombinant DNA using Escherichia coli minicells. In R. Wu & L. Grossman (Eds.), Methods in Enzymology (vol. 101, pp. 347-362). Academic Press. https://doi.org/10.1016/0076-6879(83)01023-0.

Cohn, E. J., Oncley, J. L., Strong, L. E., Hughes, W. L. Jr., & Armstrong, S. H. Jr. (1944). Chemical, clinical, and immunological studies on the products of human plasma fractionation. I. The characterization of the protein fractions of human plasma. The Journal of Clinical Investigation, 23(4), 417-432. https://doi.org/10.1172/JCI101508.

Cohn, E. J., Strong, L. E., Hughes, W. L. Jr., Mulford, D. J., Ashworth, J. N., Melin, M., & Taylor, H. L. (1946). Preparation and properties of serum and plasma proteins. IV. A system for the separation into fractions of the protein and lipoprotein components of biological tissues and fluids. Journal of the American Chemical Society, 68(3), 459-475. https://doi.org/10.1021/ja01207a034.

(56) References Cited

OTHER PUBLICATIONS

Court of Justice of the Andean Community. (n.d.). Intranet. comunidadandina.org [online]. Available no later than Apr. 18, 2019. Retrieved Dec. 21, 2022, from https://intranet.comunidadandina.org.

Crow, Andrew R et al. "Mechanisms of action of intravenous immunoglobulin in the treatment of immune thrombocytopenia." Pediatric blood & cancer vol. 47,5 Suppl (2006): 710-3. doi:10.1002/pbc.20980.

Dalziel et al., "Lectin analysis of human immunoglobulin G N-glycan sialylation," Glycoconj J., Dec. 1999, 16(12):801-807.

Destefano, A., & Hunt, D. (2012). US Pharmacopeia Proposes New Standard on Glass Quality. Pharmaceutical Technology, 68-70. PharmTech.com/usp (Year: 2012).

Dizon-Maspat et al., "Singe Pass Tangential Flow Filtration to Debottleneck Downstream Processing for Therapeutic Antibody Production," Biotechnology and Bioengineering 109(4):962-970 (2012).

Dodel et al., Intravenous Immunoglobulins as a Treatment for Alzheimer's Disease, Drugs 2010; 70(5): 513-528.

Donadio, S., Monciardini, P., & Sosio, M. (2003). Analysis of the biosynthetic gene cluster for the polyether antibiotic nanchangmycin. Biochemistry, 85(4), 311-321. https://doi.org/10.1046/j.1365-2958.2003.03571.x.

Dotz, V., Visconti, A., Lomax-Browne, H. J., Clerc, F., Hipgrave Ederveen, A. L., Medjeral-Thomas, N. R., Cook, H. T., Pickering, M. C., Wuhrer, M., & Falchi, M. (2021). O- and N-Glycosylation of serum immunoglobulin A is associated with IgA nephropathy and glomerular function. Journal of the American Society of Nephrology, 32(10), 2455-2465. https://doi.org/10.1681/ASN.2020081208.

Edelman, G M et al. "The covalent structure of an entire gammaG immunoglobulin molecule." Proceedings of the National Academy of Sciences of the United States of America vol. 63,1 (1969): 78-85. doi:10.1073/pnas.63.1.78.

Extended European Search Report for European Application No. 20792022.4, dated Nov. 10, 2022 (11 pages).

Extended European Search Report for European Application No. 21809062.9, dated Oct. 5, 2024 (7 pages).

Fernandez-Cruz et al., "6th International Immunoglobulin Symposium: poster presentations," Clin Exp Immunol., Dec. 2009, 158(Suppl 1):60-67.

Fokkink et al., "Immunoglobulin G Fc N-glycosylation in Guillain-Barre syndrome treated with intravenous immunoglobulin," Clinical and Experimental Immunology, Dec. 2014, 178(Suppl 1):105-107.

Frankish, "Lancet Asia Medical Forum—call for papers," The Lancet Neurology, Sep. 1, 2008, 7(9):P771.

Gasser B. et al. Antibody production with yeasts and filamentous fungi: on the road to large scale?, Biotechnology letters, 2007, v. 29, No. 2, pp. 201-212, p. 208.

Goh and Ng, "Impact of Host Cell Line Choice on Glycan Profile," Critical Reviews in Biotechnology 38(6):851-67 (2018).

Green & Sambrook, Molecular Cloning: A Laboratory Manual, Fourth Edition (2012) Cold Spring Harbor Laboratory Press, Cold Spring Harbor, N.Y.

Hassan, Mohamed E. et al., Impact of immobilization technology in industrial and pharmaceutical applications / 3 Biotech. Dec. 2019; 9(12):440.

Hawe, A. et al. (2013) Pharmaceutical feasibility of sub-visible particle analysis in parenterals with reduced volume light obscuration methods. European Journal of Pharmaceutics and Biopharmaceutics, 85(3), 1084-1087 (Year: 2013).

Holland et al., "Differential glycosylation of polyclonal IgG, IgG-Fc and IgG-Fab isolated from the sera of patients with ANCA-associated systemic vasculitis," Biochimica et Biophysica Acta., Apr. 2006, 1760(4):669-677.

Horowitz et al., "Strategies for Viral Inactivation," Current Opinion in Hematology 2(6):484-92 (1995).

Hughes et al., "Intravenous immune globulin (10% caprylatechromatography purified) for the treatment of chronic inflammatory demyelinating polyradiculoneuropathy (ICE study): a randomised placebo-controlled trial," Lancet Neurol., 2008; 7:136-144.

Iijima et al., "Efficacy and availability of intravenous immunoglobulin in chronic inflammatory demyelinating polyneuropathy," Nihon Rinsho., Apr. 2012, 70(4):715-721 (English Abstract Only).

Imashuku, "High dose immunoglobulin (IVIG) may reduce the incidence of Langerhans cell histiocytosis (LCH)-associated central nervous system involvement," CNS Neurol Disord Drug Targets., Nov. 2009, 8(5):380-386 (English Abstract Only).

International Preliminary Report on Patentability for International Application No. PCT/US2020/028863, dated Jul. 20, 2020 (7 pages).

International Preliminary Report on Patentability for International Application No. PCT/US2021/019607, dated Jun. 15, 2021 (10 pages).

International Preliminary Report on Patentability for International Application No. PCT/US2021/020898, dated Sep. 14, 2021 (8 pages).

International Preliminary Report on Patentability for International Application No. PCT/US2021/033150, dated Nov. 17, 2022 (6 pages).

International Preliminary Report on Patentability for International Application No. PCT/US2021/033156, dated Nov. 2, 2021 (9 pages).

International Preliminary Report on Patentability for International Application No. PCT/US2021/057658, dated Feb. 4, 2022 (9 pages).

International Preliminary Report on Patentability for International Application No. PCT/US2021/057659, dated Oct. 27, 2021 (8 pages).

International Preliminary Report on Patentability for International Application No. PCT/US2021/060182, dated May 16, 2023 (7 pages).

International Search Report and Written Opinion for International Application No. PCT/US2020/028863, dated Jul. 20, 2020, 11 pages.

International Search Report and Written Opinion for International Application No. PCT/US2021/019607, dated Jun. 15, 2021, 9 pages.

International Search Report and Written Opinion for International Application No. PCT/US2021/020898, dated Sep. 14, 2021, 7 pages.

International Search Report and Written Opinion for International Application No. PCT/US2021/033150, dated Oct. 5, 2021 (9 pages).

International Search Report and Written Opinion for International Application No. PCT/US2021/033156, dated Nov. 2, 2021, 8 pages.

International Search Report and Written Opinion for International Application No. PCT/US2021/057658, dated Feb. 4, 2022, 8 pages.

International Search Report and Written Opinion for International Application No. PCT/US2021/057659, dated Oct. 27, 2021, 7 pages.

International Search Report and Written Opinion for International Application No. PCT/US2021/060182, dated May 27, 2022, 6 pages.

Jakubke H.-D et al., Aminokisloty, peptidy, belki [Aminoacids, peptides and proteins], Moscow:Mir, 1985, pp. 92-94.

Jassal et al., "Sialylation of Human IgG-Fc Carbohydrate by Transfected Rat a2,6-Sialyltransferase," Biochemical and Biophysical Research Communications, 2001, 286:243-249.

Kanda, "Treatment of chronic inflammatory demyelinating polyradiculoneuropathy and multifocal motor neuropathy," Yamaguchi Uni. Grad.School of Med. 2017, vol. 34, No. 3,pp. 178-181.

Keskin O. et al. A new, structurally nonredundant, diverse data set of protein-protein interfaces and its implications, Protein Sci., 2004, v. 13, No. 4, pp. 1043-1055, abstract, pp. 1043-1044.

Kiese, S., Pappenberger, A., Friess, W., & Mahler, H.-C. (2008). Shaken, Not Stirred: Mechanical Stress Testing of an IgG1 Antibody. Journal of Pharmaceutical Sciences, 97(10), 4347-4366. https://doi.org/10.1002/jps.21328 (Year: 2008).

Kightlinger et al., "Synthetic Glycobiology: Parts, Systems, and Applications," ACS Synth. Biol. 9:1534-62 (2020).

Klutz et al., "Continuous Viral Inactivation at low Ph Value in Antibody Manufacturing," Chemical Engineering and Processing: Process Intensification 102:88-11 (2016).

(56) References Cited

OTHER PUBLICATIONS

Kobata, "Function and pathology of the sugar chains of human immunoglobulin G," Glycobiology, 1990, 1(1):5-8.

Kriegler, M. (1990). Gene transfer and expression: A laboratory manual. W.H. Freeman and Company.

Kuhn, Bernd et al. "The structure of human α-2,6-sialyltransferase reveals the binding mode of complex glycans." Acta crystallographica. Section D, Biological crystallography vol. 69, Pt 9 (2013): 1826-38. doi:10.1107/S0907444913015412.

Kumpel et al., "Galactosylation of human IgG monoclonal anti-D produced by EBV-transformed Blymphoblastoid cell lines is dependent on culture method and affects Fc receptor-mediated functional activity," Hum Antibodies Hybridomas., 1994, 5(3-4):143-151.

Kumar et al., "Immunoglobulin therapy in the treatment of multifocal motor neuropathy", J Neurol Sci, 2017, vol. 375, pp. 190-197.

Kurnik, "Buffer Exchange Using Size Development, and Industrial Application," Biotechnology and Bioengineering 45(2):149-58 (1995).

Lars Kober et al: "Optimized signal peptides for the development of high expressing CHO cell lines", Biotechnology and Bioengineering, John Wiley, Hoboken, USA, vol. 110, No. 4, Jan. 17, 2013 (Jan. 17, 2013), pp. 1164-1173, XP071113992, ISSN: 0006-3592, DOI: 10.1002/BIT.24776.

Leontyev et al., "Sialylation-independent mechanism involved in the amelioration of murine immune thrombocytopenia using intravenous gammaglobulin," Transfusion, Aug. 2012, 52(8):1799-805.

Liu et al., "Oriented Immobilization of Proteins on Solid Supports for Use in Biosensors and Biochips: a Review," Microchim Acta 2016; 183;1-19.

Lund et al., "Multiple Interactions of IgG with Its Core Oligosaccharide Can Modulate Recognition by Complement and Human Fcy Receptor I and Influence the Synthesis of Its Oligosaccharide Chains," J Immunol., 1996, 157:4963-4969.

Lundstrom et al., "Blood Plasma IgG Fc Glycans are Significantly Altered in Alzheimer's Disease and Progressive Mild Cognitive Impairment," Journal of Alzheimer's Disease, 2014, 38:567-579.

Malhotra et al., "Glycosylation changes of IgG associated with rheumatoid arthritis can activate complement via the mannose-binding protein," Nature Medicine, 1992, 1:237-243.

Manning, R. (May 5, 2014). Embracing complexity: Understanding IVIg to rationally design novel therapeutics [Conference presentation]. PEGS Boston.

Mayya, Viveka et al. "Quantitative phosphoproteomic analysis of T cell receptor signaling reveals system-wide modulation of protein-protein interactions." Science signaling vol. 2,84ra46. Aug. 18, 2009, doi: 10.1126/scisignal.2000007.

Mazourov et al., "The Efficacy of systemic enzyme therapy in the treatment of rheumatoid arthritis," Int J Immunotherapy., 1997, XIII(3/4):85-91.

Meldal and Schoffelen, "Recent Advances in Covalent, Site-Specific Protein Immobilization," F1000Research 216,5(F1000 Faculty Rev):2303.

Meyer et al., "Advances in DNA-Directed Immobilization," Curr Opin Chem Biol. 2014;18:8-15.

Mimura et al., "The influence of glycosylation on the thermal stability and effector function expression of human IgGI-Fc: properties of a series of truncated glycoforms," Molecular Immunology, 2000, 37(12-13):697-706.

Mohammad et al., "Nanofiltration Membranes Review: Recent Advances and Future Prospects," Desalination 356:226-54 (2015).

Morrison, D. A. (1977). Transformation in Escherichia coli: Cryogenic preservation of competent cells. Journal of Bacteriology, 132(1), 349-351. https://doi.org/10.1128/jb.132.1.349-351.1977.

National Center for Biotechnology Information (NCBI). (Jul. 16, 2007). Substance record SID 24898182. PubChem. Retrieved Dec. 15, 2022, from https://pubchem.ncbi.nlm.nih.gov/substance/24898182 pages.

National Institutes of Health (NIH). (1991). NIH publication 91-3242. National Technical Information Services.

Negre, E., et al. (n.d.). Training continued for hospital pharmacists [Machine-translated document]. Available no later than Apr. 18, 2019. Retrieved Dec. 21, 2022.

Nguyen et al., "Improved HCP Reduction Using a New, All-Synthetic Depth Filtration Media Within an Antibody Purification Process," Biotechnology Journal 14(1):1700771 (2019).

Nimmerjahn et al., "Anti-Inflammatory Actions of Intravenous Immunoglobulin," Annual Review of Immunology, 2008, 26:513-533.

Nishitsuji et al., "Apolipoprotein E regulates the integrity of tight junctions in an isoform-dependent manner in an in vitro blood-brain barrier model," J Biol Chem., 2011, 286(20):17536-17542.

Ofosu et al., "Plasma-Derived Biological Medicines Used to Promote Haemostasis," Thromb Haemost 99:851-62 (2008).

Pakula A. A. et al. Genetic analysis of protein stability and function. Anna. Rev. Genet. 1989, v. 23, pp. 289-310, pp. 305-306.

Palva, I., Lehtovaara, P., Kaariainen, L., Sibakov, M., Cantell, K., Schein, C. H., Kashiwagi, K., & Weissmann, C. (1983). Secretion of interferon by Bacillus subtilis. Gene, 22(3), 229-235. https://doi.org/10.1016/0378-1119(83)90100-0.

Paulson, J. C., & Colley, K. J. (1989). Glycosyltransferases: Structure, localization, and control of cell type-specific glycosylation. Journal of Biological Chemistry, 264(30), 17615-17618. https://doi.org/10.1016/S0021-9258(19)84926-6.

Radosevich, M., & Burnouf, T. (2010). Intravenous immunoglobulin G: Trends in production methods, quality control, and quality assurance. Vox Sanguinis, 98(1), 12-28. https://doi.org/10.1111/j.1423-0410.2009.01226.x.

Raju et al., "Glycoengineering of therapeutic glycoproteins: in vitro galactosylation and sialylation of glycoproteins with terminal N-acetylglucosamine and galactose residues," Biochemistry, Jul. 31, 2001, 40(30):8868-8876.

Raju et al., "Species-specific variation in glycosylation of IgG: evidence for the species-specific sialylation and branch-specific galactosylation and importance for engineering recombinant glycoprotein therapeutics," Glycobiology, May 1, 2000, 10(5):477-486.

Ramakrishnan, Boopathy et al. "Structural snapshots of beta-1,4-galactosyltransferase-I along the kinetic pathway." Journal of molecular biology vol. 357,5 (2006): 1619-33. doi:10.1016/j.jmb.2006.01.088.

Ramasamy, Velavan et al. "Oligosaccharide preferences of beta1,4-galactosyltransferase-I: crystal structures of Met340His mutant of human beta1,4-galactosyltransferase-I with a pentasaccharide and trisaccharides of the N-glycan moiety." Journal of molecular biology vol. 353,1 (2005): 53-67. doi:10.1016/j.jmb.2005.07.050.

Ramos-de-la-Pena et al., "Protein A Chromatography: Challenges and Process in the Purification of Monoclonal Antibodies," Journal of Separation Science 2019:doi:10.1002/jssc.201800963.

Sambrook, Fritsch & Maniatis, Molecular Cloning: A Laboratory Manual, Third Edition (2001) Cold Spring Harbor Laboratory Press, Cold Spring Harbor, N.Y.

Samuelsson et al., "Anti-inflammatory activity of IVIG mediated through the inhibitory Fc receptor," Science, 2001, 291:484-486.

Sapsford et al., "Functionalizing Nanoparticles with Biological Molecules: Developing Chemistries that Facilitate Nanotechnology," Chem Rev. 2013;113(3)1904-2074.

Scallon et al., "Higher levels of sialylated Fc glycans in immunoglobulin G molecules can adversely impact functionality," Mol Immunol., 2007, 44(7):524-1534.

Scielo.org.ve. (Dec. 2006). Fronesis. Retrieved Feb. 10, 2023, from http://www.scielo.org.ve/scielo.php?script=sci_arttext&pid=S1315-62682006000300002&lng=es&nrm=iso.

Seffernick J. L. et al. Melamine Deaminase and Atrazine Chlorohydrolase: 98 Percent Identical but Functionally Different, Journal of Bacteriology, 2001, v. 183, No. 8, pp. 2405-2410, abstract.

Shen J. et al. Single variable domain-IgG fusion: a novel recombinant approach to Fc domain containing bispecific antibodies, Journal of Biological Chemistry, 2006, v. 281, No. 16, pp. 10706-10714, p. 10713.

Smith, T. F., & Waterman, M. S. (1981). Identification of common molecular subsequences. Journal of Molecular Biology, 147(1), 195-197. https://doi.org/10.1016/0022-2836(81)90087-5.

(56)　　　　　References Cited

OTHER PUBLICATIONS

Sorina Morar-Mitrica, Puri, M., Sassi, A. B., Fuller, J., Hu, P., Crotts, G., & Nesta, D. (2015). Development of a stable low-dose aglycosylated antibody formulation to minimize protein loss during intravenous administration. Mabs, 7(4), 792-803. https://doi.org/10. 1080/19420862.2015.1046664 (year: 2015).

Steen et al., "Protein Engineering for Directed Immobilization," Bioconjug Chem. 2013;24(11):1761-77.

Sudo et al., "Different IVIG Glycoforms Affect In Vitro Inhibition of Anti-Ganglioside Antibody-Mediated 75*Complement Deposition," PLoS One, 2014, 9(9):e107772.

Sutherland, "Filtration Overview: A Closer Look at Depth Filtration," Filtration and Separation 45(8)25-28 (2008).

Tokuriki N. et al. Stability effects of mutations and protein evolvability, Curr. Opin. Struct. Biol., 2009, v. 19, No. 5, pp. 596-604, pp. 596, 598, 602.

Trilling et al., "Antibody Orientation on Biosensor Surfaces: a Minireview," Analyst 2013;138(6):1619-27.

Wang et al., "Antibody structure, instability, and formulation," Journal of Pharmaceutical Sciences, Jan. 2007, 96(1):1-26.

Wang, "Instability, stabilization, and formulation of liquid protein pharmaceuticals," International Journal of Pharmaceutics, Aug. 1999, 185(2):129-188.

Warne, "Development of high concentration protein biopharmaceuticals: The use of platform approaches in formulation development," European Journal of Pharmaceutics and Biopharmaceutics, Jun. 2011, 78(2):208-212.

Washburn et al., "High-resolution physicochemical characterization of different intravenous immunoglobulin products," PLoS One, 2017, 12(7):e0181251.

Whisstock J. C. et al., "Prediction of protein function from protein sequence and structure", Quarterly Reviews of Biophysics 36, 2003, p. 307-340. DOI: 10.1017/S0033583503003901 (see p. 313 para. 4, p. 323 para. 1).

Wikipedia contributors. (n.d.). Medicine. Wikipedia. Retrieved Dec. 21, 2022, from https://es.wikipedia.org/wiki/Medicamento.

Witkowski A. et al. Conversion of a β-Ketoacyl Synthase to a Malonyl Decarboxylase by Replacement of the Active-Site Cysteine with Glutamine. Biochemistry, 1999, v. 38, No. 36, pp. 11643-11650, abstract, Table. 1.

Wong et al., "Sialylated IgG-Fc: a novel biomarker of chronic inflammatory demyelinating polyneuropathy," J Neurol Neurosurg Psychiatry., 2016, 87:275-279.

Yampolsky L. Y. et al. The exchangeability of amino acids in proteins, Genetics, 2005, v. 170, No. 4, pp. 1459-1472, abstract, p. 1465, Table 3.

Zufferey et al., "Woodchuck Hepatitis Virus Posttranscriptional Regulatory Element Enhances Expression of Transgenes Delivered by Retroviral Vectors," Journal of Virology 73(4):2886-92 (1999).

U.S. Appl. No. 17/284,188, filed Apr 9, 2021.

U.S. Appl. No. 14/416,869, filed Jan. 23, 2015.

U.S. Appl. No. 15/957,703, filed Apr. 19, 2018.

U.S. Appl. No. 17/508,026, filed Oct. 22, 2021.

U.S. Appl. No. 14/787,403, filed Oct. 27, 2015.

U.S. Appl. No. 15/954,146, filed Apr. 16, 2018.

U.S. Appl. No. 16/589,634, filed Oct. 1, 2019.

U.S. Appl. No. 17/033,452, filed Sep. 25, 2020.

U.S. Appl. No. 17/032,994, filed Sep. 25, 2020.

U.S. Appl. No. 17/100,428, filed Nov. 20, 2020.

U.S. Appl. No. 18/217,401, filed Jun. 30, 2023.

U.S. Appl. No. 18/022,061, filed Feb. 17, 2023.

U.S. Appl. No. 18/218,996, filed Jul. 6, 2023.

U.S. Appl. No. 15/028,917, filed Apr. 12, 2016.

U.S. Appl. No. 15/985,288, filed May 21, 2018.

U.S. Appl. No. 16/688,772, filed Nov. 19, 2019.

U.S. Appl. No. 18/136,803, filed Apr. 19, 2023.

U.S. Appl. No. 14/890,865, filed Nov. 12, 2015.

U.S. Appl. No. 16/671,595, filed Nov. 1, 2019.

U.S. Appl. No. 17/739,912, filed May 9, 2022.

U.S. Appl. No. 17/602,156, filed Oct. 7, 2021.

U.S. Appl. No. 17/925,999, filed Nov. 17, 2022.

U.S. Appl. No. 17/802,441, filed Aug. 25, 2022.

U.S. Appl. No. 17/926,102, filed Nov. 17, 2022.

U.S. Appl. No. 17/909,282, filed Sep. 2, 2022.

U.S. Appl. No. 18/022,069, filed Feb. 17, 2023.

U.S. Appl. No. 18/037,378, filed May 17, 2023.

B4GT1_HUMAN, accession No. P15291, Uniprot, entry version 5 published Dec. 11, 2019, obtained from <https://rest.uniprot.org/unisave/P15291?format=txt&versions=215>; hereafter "B4GT1_HUMAN" (Year: 2019).

Bowie et al. (Science, 247:1306-1310, 1990) (Year: 1990).

Dalakas, Marinos et al., "Subcutaneous IgG for chronic inflammatory demylinating polyneuropathy", The Lancet Neurology, vol. 17, No. 1, Jan. 2018 (Jan. 2018), pp. 20-21, XP085320330, ISSN: 1474-4422, DOI: 10.1016/S1474-4422 (17) 30379-4.

Deb et al. Bacterial expression, correct membrane targeting and functional folding of the HIV-1 membrane protein Vpu using a perplasmic signal peptide, PLoS One, published Feb. 22, 2017, vol. 12, No. 2 (Year: 2017).

Gevaert et al., Gel-Free Proteomics: Methods and Protocols, Humana Press, Ch 20, pp. 299-308 (Year 2011).

Gramer et al. (Biotechnical Bioeng. Jul. 2011;108(7):1591-602. doi: 10.1002/bit.23075. Epub Feb. 18, 2011) (Year: 2011).

Harrus et al., The dimeric structure of wild-type human glycosyltransferase B4GalT1, PLoS One, published Oct. 23, 2018, vol. 13, No. 10 (Year: 2018).

Hopax (The families of biological buffers, obtained from: https://www.hopaxfc.come/en/blog/the-families-of-biological-buffers (Jan. 22, 2019)) (Year :2019).

Ishida (Effects of point mutation on enzymatic activity: correlation between protein electronic structure and motion in chorismate mutase reaction. J Am Chem Soc. May 26, 2010; 132(20):7104-18. doi: 10.1021/ja100744h) (Year: 2010).

Kurogochi, Masaki et al., "Relative Quantitation of Flycopeptides Based on Stable Isotope Labeling Using MALDI-TOF MS", Molecules, Jul. 9, 2014, vol. 19, No. 7, p. 9944-9961, DOI: 10.3390/molecules19079944.

Laroy et al., Characterization of sialyltransferase mutants using surface plasmon resonance, Glycogiology, published Mar. 1, 2001, vol. 11, No. 3, p. 175-182 (Year: 2001).

Lazar et al. (Molecular and Cellular Biology. 1988; 8(3): 1247-1252) (Year: 1988).

LCGC Asia Pacific—Jun. 1, 2007, obtained from: https://www.chromatographyonline.come/view/butter-preparation-hints-tips-and-common-errors-0) (Year: 2007).

Lewis et al. (α-2,3-Sialyltransferase Expression Level Impacts the Kinetics of Lipooligosaccharide Sialylation, Complement Resistance, and the Ability of Neisseria gonorrhoeae to Colonize the Murine Genital Tract. mBio 6:10.1128/mbio.02465-14) (Year: 2015).

Nagwa teaches that (Question Video: Identifying Possible Effects of a Mutation on the Active Site of an Enzyme, obtained from: http://web.archive.org/web/20210120131812/https://www.nagwa.com/en/videos/450142461549/, available as of Jan. 29, 2021 as evidenced by Wayback Machine) (Year: 2021).

Olczak et al., Comparison of different signal peptides for protein secretion in nonlytic insect cell system, Analytical Biochemistry, published 2006, vol. 359, p. 45-53 (Year: 2006).

Ritter, Christian et al., "Chronic inflammatory demyelinating polyneuropathy (CIDP): change of serum IgG dimer levels during treatment with intravenous immunoglobulins", Journal of Neuroinflamation, Biomed Central Ltd., London, GB, vol. 12, No. 1, Aug. 14, 2015 (Aug. 14, 2015), p. 148, XP021228661, ISSN: 1742-2094, DOI: 10.1186/S12974-015-0361-1.

Roy, Rini et al., "Absolute Quantitation of Glycoforms of Two Human IgG Subclasses Using Synthetic Fc Peptides and Glycopeptides", Journal of the American Society for Mass Spectrometry, May 23, 2018, vol. 29, No. 6, p. 1086-1098, DOI: 10.1007/s13361-018-1900-7.

SIAT1_HUMAN, accession No. P15907, Uniprot, entry version 194 published Jan. 16, 2019, obtained from <https://rest.uniprot.org/unisave/P15907?format=txt&versions=194>; (Year: 2019).

Sinha, Sandipan et al., "Comparison of LC and LC/MS methods for quantifying N-glycosylation in recombinant IgGs", Journal of the

(56) References Cited

OTHER PUBLICATIONS

American Society for Mass Spectrometry, Nov. 1, 2008, vol. 19, No. 11, p. 1643-1654, DOI: 10.1016/j.jasms.2008.07.004.
Soliven B.: "Animal Models of Autoimmune Neuropathy", Ilar Journal, vol. 54, No. 3, Jan. 1, 2014 (Jan. 1, 2014), pp. 282-290, XP093301065, US ISSN: 1084-2020, DOI: 10:1093/ilar/ilt054.

\* cited by examiner

MTRLTVLALLAGLLASSRAGSSPLLAMEWSHPQFEKLEGGGSGGGSGGSWSHPQ
FEKHAHAHSRKDHLIHNVHKEEHAHAHNKELGTAVFQGPMRRAIRGRSFQVWNKD
SSSKNLIPRLQKIWKNYLSMNKYKVSYKGPGPGIKFSAEALRCHLRDHVNVSMVEV
TDFPFNTSEWEGYLPKESIRTKAGPWGRCAVVSSAGSLKSSQLGREIDDHDAVLR
FNGAPTANFQQDVGTKTTIRLMNSQLVTTEKRFLKDSLYNEGILIVWDPSVYHSDIP
KWYQNPDYNFFNNYKTYRKLHPNQPFYILKPQMPWELWDILQEISPEEIQPNPPSS
GMLGIIIMMTLCDQVDIYEFLPSKRKTDVCYYQKFFDSACTMGAYHPLLYEKNLVK
HLNQGTDEDIYLLGKATLPGFRTIHCPG   SEQ ID NO: 1

FIG. 1A

GSYYDSFKLQTKEFQVLKSLGKLAMGSDSQSVSSSSTQDPHRGRQTLGSLRGLAK
AKPEASFQVWNKDSSSKNLIPRLQKIWKNYLSMNKYKVSYKGPGPGIKFSAEALRC
HLRDHVNVSMVEVTDFPFNTSEWEGYLPKESIRTKAGPWGRCAVVSSAGSLKSSQ
LGREIDDHDAVLRFNGAPTANFQQDVGTKTTIRLMNSQLVTTEKRFLKDSLYNEGILI
VWDPSVYHSDIPKWYQNPDYNFFNNYKTYRKLHPNQPFYILKPQMPWELWDILQEI
SPEEIQPNPPSSGMLGIIIMMTLCDQVDIYEFLPSKRKTDVCYYQKFFDSACTMGA
YHPLLYEKNLVKHLNQGTDEDIYLLGKATLPGFRTIHC     SEQ ID NO: 2

FIG. 1B

MIHTNLKKKFSYFILAFLLFALICVWKKGSYEALKLQAKEFQVTKSLEKLAIGSGSQS
TSASIKQDSKPGSQVLSHLRVTAKVKPQSPYQVWDKNSSSKNLNPRLQKILKNYLS
MNKYKVSYKGPGPGVKFSVEALRCHLRDRVNVSMIEATDFPFNTTEWEGYLPKEN
FRTKAGPWHRCAVVSSAGSLKSSHLGKEIDSHDAVLRFNGAPVADFQQDVGMKTT
IRLMNSQLITTEKQFLKDSLYNEGILIVWDPSLYHADIPNWYKKPDYNFFETYKSYRK
LYPSQPFYILRPQMPWELWDIIQEIAPDRIQPNPPSSGMLGIIIMMTLCDQVDVYEFL
PSKRKTDVCYYHQKFFDSACTMGAYHPLLFEKNMVKQLNEGTDEDIYIFGKATLSG
FRTIHC   SEQ ID NO: 3

FIG. 1C

SEQUENCE LISTING

```
<160> NUMBER OF SEQ ID NOS: 3

<210> SEQ ID NO 1
<211> LENGTH: 418
<212> TYPE: PRT
<213> ORGANISM: Homo sapiens

<400> SEQUENCE: 1

Met Thr Arg Leu Thr Val Leu Ala Leu Leu Ala Gly Leu Leu Ala Ser
1               5                   10                  15

Ser Arg Ala Gly Ser Ser Pro Leu Leu Ala Met Glu Trp Ser His Pro
            20                  25                  30

Gln Phe Glu Lys Leu Glu Gly Gly Gly Ser Gly Gly Gly Ser Gly Gly
        35                  40                  45

Ser Trp Ser His Pro Gln Phe Glu Lys His Ala His Ala His Ser Arg
    50                  55                  60

Lys Asp His Leu Ile His Asn Val His Lys Glu Glu His Ala His Ala
65                  70                  75                  80

His Asn Lys Glu Leu Gly Thr Ala Val Phe Gln Gly Pro Met Arg Arg
                85                  90                  95

Ala Ile Arg Gly Arg Ser Phe Gln Val Trp Asn Lys Asp Ser Ser Ser
            100                 105                 110

Lys Asn Leu Ile Pro Arg Leu Gln Lys Ile Trp Lys Asn Tyr Leu Ser
            115                 120                 125

Met Asn Lys Tyr Lys Val Ser Tyr Lys Gly Pro Gly Pro Gly Ile Lys
        130                 135                 140

Phe Ser Ala Glu Ala Leu Arg Cys His Leu Arg Asp His Val Asn Val
145                 150                 155                 160

Ser Met Val Glu Val Thr Asp Phe Pro Phe Asn Thr Ser Glu Trp Glu
                165                 170                 175

Gly Tyr Leu Pro Lys Glu Ser Ile Arg Thr Lys Ala Gly Pro Trp Gly
            180                 185                 190

Arg Cys Ala Val Val Ser Ser Ala Gly Ser Leu Lys Ser Ser Gln Leu
            195                 200                 205

Gly Arg Glu Ile Asp Asp His Asp Ala Val Leu Arg Phe Asn Gly Ala
        210                 215                 220

Pro Thr Ala Asn Phe Gln Gln Asp Val Gly Thr Lys Thr Thr Ile Arg
225                 230                 235                 240

Leu Met Asn Ser Gln Leu Val Thr Thr Glu Lys Arg Phe Leu Lys Asp
                245                 250                 255

Ser Leu Tyr Asn Glu Gly Ile Leu Ile Val Trp Asp Pro Ser Val Tyr
            260                 265                 270

His Ser Asp Ile Pro Lys Trp Tyr Gln Asn Pro Asp Tyr Asn Phe Phe
            275                 280                 285
```

```
Asn Asn Tyr Lys Thr Tyr Arg Lys Leu His Pro Asn Gln Pro Phe Tyr
    290                 295                 300

Ile Leu Lys Pro Gln Met Pro Trp Glu Leu Trp Asp Ile Leu Gln Glu
305                 310                 315                 320

Ile Ser Pro Glu Glu Ile Gln Pro Asn Pro Pro Ser Ser Gly Met Leu
                325                 330                 335

Gly Ile Ile Ile Met Met Thr Leu Cys Asp Gln Val Asp Ile Tyr Glu
                340                 345                 350

Phe Leu Pro Ser Lys Arg Lys Thr Asp Val Cys Tyr Tyr Tyr Gln Lys
                355                 360                 365

Phe Phe Asp Ser Ala Cys Thr Met Gly Ala Tyr His Pro Leu Leu Tyr
        370                 375                 380

Glu Lys Asn Leu Val Lys His Leu Asn Gln Gly Thr Asp Glu Asp Ile
385                 390                 395                 400

Tyr Leu Leu Gly Lys Ala Thr Leu Pro Gly Phe Arg Thr Ile His Cys
                405                 410                 415

Pro Gly

<210> SEQ ID NO 2
<211> LENGTH: 375
<212> TYPE: PRT
<213> ORGANISM: Homo sapiens

<400> SEQUENCE: 2

Gly Ser Tyr Tyr Asp Ser Phe Lys Leu Gln Thr Lys Glu Phe Gln Val
1               5                   10                  15

Leu Lys Ser Leu Gly Lys Leu Ala Met Gly Ser Asp Ser Gln Ser Val
                20                  25                  30

Ser Ser Ser Ser Thr Gln Asp Pro His Arg Gly Arg Gln Thr Leu Gly
        35                  40                  45

Ser Leu Arg Gly Leu Ala Lys Ala Lys Pro Glu Ala Ser Phe Gln Val
        50                  55                  60

Trp Asn Lys Asp Ser Ser Ser Lys Asn Leu Ile Pro Arg Leu Gln Lys
65                  70                  75                  80

Ile Trp Lys Asn Tyr Leu Ser Met Asn Lys Tyr Lys Val Ser Tyr Lys
                85                  90                  95

Gly Pro Gly Pro Gly Ile Lys Phe Ser Ala Glu Ala Leu Arg Cys His
            100                 105                 110

Leu Arg Asp His Val Asn Val Ser Met Val Glu Val Thr Asp Phe Pro
        115                 120                 125

Phe Asn Thr Ser Glu Trp Glu Gly Tyr Leu Pro Lys Glu Ser Ile Arg
        130                 135                 140

Thr Lys Ala Gly Pro Trp Gly Arg Cys Ala Val Val Ser Ser Ala Gly
145                 150                 155                 160

Ser Leu Lys Ser Ser Gln Leu Gly Arg Glu Ile Asp Asp His Asp Ala
            165                 170                 175

Val Leu Arg Phe Asn Gly Ala Pro Thr Ala Asn Phe Gln Gln Asp Val
            180                 185                 190

Gly Thr Lys Thr Thr Ile Arg Leu Met Asn Ser Gln Leu Val Thr Thr
            195                 200                 205

Glu Lys Arg Phe Leu Lys Asp Ser Leu Tyr Asn Glu Gly Ile Leu Ile
        210                 215                 220

Val Trp Asp Pro Ser Val Tyr His Ser Asp Ile Pro Lys Trp Tyr Gln
225                 230                 235                 240
```

-continued

```
Asn Pro Asp Tyr Asn Phe Phe Asn Asn Tyr Lys Thr Tyr Arg Lys Leu
            245             250             255

His Pro Asn Gln Pro Phe Tyr Ile Leu Lys Pro Gln Met Pro Trp Glu
            260             265             270

Leu Trp Asp Ile Leu Gln Glu Ile Ser Pro Glu Glu Ile Gln Pro Asn
            275             280             285

Pro Pro Ser Ser Gly Met Leu Gly Ile Ile Ile Met Met Thr Leu Cys
            290             295             300

Asp Gln Val Asp Ile Tyr Glu Phe Leu Pro Ser Lys Arg Lys Thr Asp
305             310             315             320

Val Cys Tyr Tyr Tyr Gln Lys Phe Phe Asp Ser Ala Cys Thr Met Gly
            325             330             335

Ala Tyr His Pro Leu Leu Tyr Glu Lys Asn Leu Val Lys His Leu Asn
            340             345             350

Gln Gly Thr Asp Glu Asp Ile Tyr Leu Leu Gly Lys Ala Thr Leu Pro
            355             360             365

Gly Phe Arg Thr Ile His Cys
    370             375

<210> SEQ ID NO 3
<211> LENGTH: 402
<212> TYPE: PRT
<213> ORGANISM: Homo sapiens

<400> SEQUENCE: 3

Met Ile His Thr Asn Leu Lys Lys Lys Phe Ser Tyr Phe Ile Leu Ala
1               5               10              15

Phe Leu Leu Phe Ala Leu Ile Cys Val Trp Lys Lys Gly Ser Tyr Glu
            20              25              30

Ala Leu Lys Leu Gln Ala Lys Glu Phe Gln Val Thr Lys Ser Leu Glu
            35              40              45

Lys Leu Ala Ile Gly Ser Gly Ser Gln Ser Thr Ser Ala Ser Ile Lys
    50              55              60

Gln Asp Ser Lys Pro Gly Ser Gln Val Leu Ser His Leu Arg Val Thr
65              70              75              80

Ala Lys Val Lys Pro Gln Ser Pro Tyr Gln Val Trp Asp Lys Asn Ser
            85              90              95

Ser Ser Lys Asn Leu Asn Pro Arg Leu Gln Lys Ile Leu Lys Asn Tyr
            100             105             110

Leu Ser Met Asn Lys Tyr Lys Val Ser Tyr Lys Gly Pro Gly Pro Gly
            115             120             125

Val Lys Phe Ser Val Glu Ala Leu Arg Cys His Leu Arg Asp Arg Val
    130             135             140

Asn Val Ser Met Ile Glu Ala Thr Asp Phe Pro Phe Asn Thr Thr Glu
145             150             155             160

Trp Glu Gly Tyr Leu Pro Lys Glu Asn Phe Arg Thr Lys Ala Gly Pro
            165             170             175

Trp His Arg Cys Ala Val Val Ser Ser Ala Gly Ser Leu Lys Ser Ser
            180             185             190

His Leu Gly Lys Glu Ile Asp Ser His Asp Ala Val Leu Arg Phe Asn
            195             200             205

Gly Ala Pro Val Ala Asp Phe Gln Gln Asp Val Gly Met Lys Thr Thr
    210             215             220

Ile Arg Leu Met Asn Ser Gln Leu Ile Thr Thr Glu Lys Gln Phe Leu
```

-continued

```
225              230              235              240

Lys Asp Ser Leu Tyr Asn Glu Gly Ile Leu Ile Val Trp Asp Pro Ser
                245              250              255

Leu Tyr His Ala Asp Ile Pro Asn Trp Tyr Lys Lys Pro Asp Tyr Asn
            260              265              270

Phe Phe Glu Thr Tyr Lys Ser Tyr Arg Lys Leu Tyr Pro Ser Gln Pro
            275              280              285

Phe Tyr Ile Leu Arg Pro Gln Met Pro Trp Glu Leu Trp Asp Ile Ile
    290              295              300

Gln Glu Ile Ala Pro Asp Arg Ile Gln Pro Asn Pro Pro Ser Ser Gly
305              310              315              320

Met Leu Gly Ile Ile Ile Met Met Thr Leu Cys Asp Gln Val Asp Val
                325              330              335

Tyr Glu Phe Leu Pro Ser Lys Arg Lys Thr Asp Val Cys Tyr Tyr His
            340              345              350

Gln Lys Phe Phe Asp Ser Ala Cys Thr Met Gly Ala Tyr His Pro Leu
            355              360              365

Leu Phe Glu Lys Asn Met Val Lys Gln Leu Asn Glu Gly Thr Asp Glu
    370              375              380

Asp Ile Tyr Ile Phe Gly Lys Ala Thr Leu Ser Gly Phe Arg Thr Ile
385              390              395              400

His Cys
```

GLYCOPROTEINS WITH ANTI-INFLAMMATORY PROPERTIES

CROSS-REFERENCE TO RELATED APPLICATIONS

This application is a continuation of U.S. application Ser. No. 15/957,703, filed on Apr. 19, 2018, now abandoned, which is a continuation of U.S. application Ser. No. 14/416, 869, filed on Jan. 23, 2015, now abandoned, which is a U.S. national stage under 35 USC § 371 of International Application Number PCT/US2013/052040, filed on Jul. 25, 2013, which claims the benefit to U.S. Provisional Application Nos. 61/676,253, filed Jul. 26, 2012 and 61/768,027, filed Feb. 22, 2013, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 20, 2021, is named Sequence_Listing.txt and is 10,812 bytes in size.

BACKGROUND

Therapeutic glycoproteins are an important class of therapeutic biotechnology products, and therapeutic Fc containing glycoproteins, such as IVIG, Fc-receptor fusions, and antibodies (including murine, chimeric, humanized and human antibodies and fragments thereof) account for the majority of therapeutic biologic products.

SUMMARY

The invention encompasses the discovery that Fc-containing glycoproteins comprising branched glycans that are sialylated on an α1-3 arm of the branched glycan in the Fc region, e.g., with a NeuAc-α2,6-Gal terminal linkage, exhibit improved anti-inflammatory properties, e.g., relative to a reference glycoprotein. Accordingly, the present disclosure encompasses such glycoproteins, as well as methods of making and methods of using such glycoproteins.

In one aspect, the invention features a method of producing a pharmaceutical preparation including glycoproteins having an Fc region, wherein the branched glycans on the Fc region are selectively sialylated on the α1-3 arm at a predetermined level. This method includes: contacting a sialyltransferase enzyme with a preparation including glycoproteins having an IgG Fc region under conditions suitable for sialylation of a plurality of the branched glycans by the enzyme; measuring the level of branched glycans having a sialic acid on the α1-3 arm and/or on the α1-6 arm; processing the preparation into a pharmaceutical preparation if the level is equivalent to the predetermined level; thereby producing a pharmaceutical preparation including glycoproteins having an Fc region, wherein the branched glycans on the Fc region are selectively sialylated on the α1-3 arm at a predetermined level.

In some embodiments, the predetermined level is at least 95% (e.g., at least 96%, 97%, 98%, 99%, up to and including 100%) of branched glycans having a sialic acid on the α1-3 arm. In other embodiments, the predetermined level is 20-90% (e.g., 20-30%, 25-35%, 30-40%, 35-45%, 40-50%, 45-55%, 50-60%, 55-65%, 60-70%, 65-75%, 70-80%, 75-85%, 80-90%) of branched glycans having a sialic acid on the α1-3 arm.

In certain embodiments, the sialyltransferase enzyme is a ST6Gal-I enzyme.

In further embodiments, the α1,3 arm of the branched glycans are sialylated with a NeuAc-α2,6-Gal terminal linkage.

In another aspect, the invention features a method of increasing anti-inflammatory activity of a reference glycoprotein preparation. This method includes: providing a reference glycoprotein preparation including glycoproteins having an IgG Fc region; and silylating the branched glycans on the Fc region on the α1-3 arm of a plurality of the branched glycans to produce a sialylated glycoprotein preparation; wherein the glycoproteins in the reference glycoprotein preparation are not IgG glycoproteins or do not consist essentially of an Fc region derived from IgG glycoproteins; and wherein the sialylated glycoprotein preparation has an increased level of anti-inflammatory activity relative to the level of anti-inflammatory activity of the reference glycoprotein preparation.

In some embodiments, the method further includes measuring in the sialylated glycoprotein preparation the level of the branched glycans having a sialic acid on the α1-3 arm and/or measuring the level of the branched glycans having a sialic acid on the α1-6 arm. In other embodiments, the method further includes processing the sialylated glycoprotein preparation into a pharmaceutical preparation if the level of branched glycans having a sialic acid on the α1-3 arm and/or the level of branched glycans having a sialic acid on the α1-6 arm meets a predetermined level (e.g., at least about 20%, 25%, 30%, 35%, 40%, 45%, 50%, 55%, 60%, 65%, 70%, 75%, 80%, 85%, 90%, 95%, or 100% of the branched glycans having a sialic acid on the α1,3 arm and/or less than about 40%, 35%, 30%, 25%, 20%, 15%, 10%, 5%, or less of the branched glycans having a sialic acid on the α1,6 arm).

In another aspect, the invention features a method of increasing anti-inflammatory activity of a reference glycoprotein preparation. This method includes: providing a reference glycoprotein preparation including glycoproteins having an IgG Fc region; and sialylating the branched glycans on the Fc region on the α1-3 arm of a plurality of the branched glycans to produce a sialylated glycoprotein preparation; measuring in the sialylated glycoprotein preparation the level of the branched glycans having a sialic acid on the α1-3 arm and/or measuring the level of the branched glycans having a sialic acid on the α1-6 arm; and processing the sialylated glycoprotein preparation into a pharmaceutical preparation if the level of branched glycans having a sialic acid on the α1-3 arm and/or the level of branched glycans having a sialic acid on the α1-6 arm meets a predetermined level; wherein the sialylated glycoprotein preparation has an increased level of anti-inflammatory activity relative to the level of anti-inflammatory activity of the reference glycoprotein preparation.

In some embodiments, the predetermined level of branched glycans having a sialic acid on the α1-3 arm is at least 95% (e.g., at least 96%, 97%, 98%, 99%, up to and including 100%) and said predetermined level of branched glycans having a sialic acid on the α1-6 arm is less than 5%. In other embodiments, the predetermined level of branched glycans having a sialic acid on the α1-3 arm is between 20-90% (e.g., 20-30%, 25-35%, 30-40%, 35-45%, 40-50%, 45-55%, 50-60%, 55-65%, 60-70%, 65-75%, 70-80%, 75-85%, 80-90%).

In some embodiments, the sialylated glycoprotein preparation has a level of anti-inflammatory activity that is at least about 10%, 20%, 30%, 40%, 50%, 60%, 70%, 80%, 90%, 100%, 125%, 150%, 175%, 200%, 300%, 400%, 500%, or more, higher than the level of anti-inflammatory activity of the reference glycoprotein preparation.

In another aspect, the invention features a method of manufacturing a pharmaceutical product including glycoproteins having an IgG Fc region. This method includes: providing a preparation including glycoproteins having an IgG Fc region; measuring the level of branched glycans on the Fc region in the preparation having a sialic acid on the α1-3 arm and/or on the α1-6 arm; and processing the preparation into a pharmaceutical product if the level of the branched glycans having a sialic acid on the α1-3 arm and/or on the α1-6 arm is equivalent to a predetermined level, thereby manufacturing a pharmaceutical product including glycoproteins having an IgG Fc region.

In some embodiments, the predetermined level is a pharmaceutical specification of greater than 25% (e.g., greater than 25%, 30%, 35%, 40%, 45%, 50%, 55%, 60%, 65%, 70%, 75%, 80%, 85%, 90%, 95%, 96%, 97%, 98%, 99%, up to and including 100%) branched glycans having a sialic acid on the α1-3 arm and/or less than 40% (e.g., less than 40%, 35%, 30%, 25%, 20%, 15%, 10%, 5%, 4%, 3%, 2%, 1%) branched glycans having a sialic acid on the α1-6 arm.

In other embodiments, the method further includes measuring (e.g., in vivo or in vitro) an anti-inflammatory activity of the preparation.

In some embodiments of any of the foregoing methods, the preparation is a preparation of antibodies.

In other embodiments of any of the foregoing methods, the preparation is formulated for intravenous or subcutaneous administration.

In certain embodiments of any of the foregoing methods, the glycoproteins are present in the preparation at a concentration of 50-250 mg/mL.

In further embodiments, the glycoproteins consist essentially of an Fc region.

In other embodiments of any of the foregoing methods, the glycoproteins further have a Fab region.

In some embodiments of any of the foregoing methods, the glycoproteins are derived from plasma.

In certain embodiments of any of the foregoing methods, the glycoproteins are recombinant glycoproteins.

In further embodiments, the glycoproteins are IgG glycoproteins or said glycoproteins consist essentially of an Fc region derived from IgG glycoproteins.

In another aspect, the invention features a pharmaceutical preparation including sialylated glycoproteins produced by any of the foregoing methods.

In another aspect, the invention features a pharmaceutical preparation including glycoproteins having an Fc region, wherein at least 95% (e.g., at least 96%, 97%, 98%, 99%, up to and including 100%) of branched glycans on the Fc region have a sialic acid on the α1-3 arm and do not have a sialic acid on the α1-6 arm, and wherein the pharmaceutical preparation has anti-inflammatory activity.

In another aspect, the invention features a pharmaceutical preparation including glycoproteins having an Fc region, wherein 20-90% (e.g., 20-30%, 25-35%, 30-40%, 35-45%, 40-50%, 45-55%, 50-60%, 55-65%, 60-70%, 65-75%, 70-80%, 75-85%, 80-90%) of branched glycans on the Fc region have a sialic acid on the α1-3 arm and do not have a sialic acid on the α1-6 arm, and wherein the pharmaceutical preparation has anti-inflammatory activity.

In another aspect, the invention features a pharmaceutical preparation including a plurality of glycoproteins having an IgG Fc region, wherein the IgG Fc region of each of the plurality of glycoproteins includes a first branched glycan sialylated on the α1-3 arm, and wherein the pharmaceutical preparation has anti-inflammatory activity.

In some embodiments, the IgG Fc region of the plurality of glycoproteins further comprises a second branched glycan. In other embodiments, the IgG Fc region of the plurality of glycoproteins further comprises a high mannose glycan. In certain embodiments, the IgG Fc region of the plurality of glycoproteins further comprises a second branched glycan sialylated on the α1-3 arm. In further embodiments, the IgG Fc region of the plurality of glycoproteins further comprises a second branched glycan sialylated on the α1-6 arm.

In some embodiments, the plurality of glycoproteins having an IgG Fc region includes at least about 20%, 25%, 30%, 35%, 40%, 45%, 50%, 55%, 60%, 65%, 70%, 75%, 80%, 85%, 90%, 95%, or 100% of the glycoproteins in the pharmaceutical preparation.

In certain embodiments of any of the foregoing pharmaceutical preparations, the pharmaceutical preparation has a level of anti-inflammatory activity that is at least about 10%, 20%, 30%, 40%, 50%, 60%, 70%, 80%, 90%, 100%, 125%, 150%, 175%, 200%, 300%, 400%, 500%, or more, higher than a level of anti-inflammatory activity of a reference glycoprotein preparation.

In other embodiments of any of the foregoing pharmaceutical preparations, the pharmaceutical preparation is a preparation of antibodies.

In some embodiments of any of the foregoing pharmaceutical preparations, the pharmaceutical preparation is formulated for subcutaneous administration.

In certain embodiments of any of the foregoing pharmaceutical preparations, the glycoproteins are present in said preparation at a concentration of 50-250 mg/mL.

In further embodiments of any of the foregoing pharmaceutical preparations, the glycoproteins consist essentially of an Fc region.

In other embodiments of any of the foregoing pharmaceutical preparations, the glycoproteins further have a Fab region.

In some embodiments of any of the foregoing pharmaceutical preparations, the glycoproteins are derived from plasma.

In certain embodiments of any of the foregoing pharmaceutical preparations, the glycoproteins are recombinant glycoproteins.

In further embodiments of any of the foregoing pharmaceutical preparations, the glycoproteins are IgG glycoproteins or said glycoproteins consist essentially of an Fc region derived from IgG glycoproteins.

In some embodiments, the pharmaceutical preparations of the invention have increased efficacy in the treatment of rheumatoid arthritis, X-linked agammagloulinemia, hypogammaglobulinemia, an acquired compromised immunity condition, immune thrombocytopenia, Kawasaki disease, allogeniec bone marrow transplant, chronic lymphocytic leukemia, common variable immunodeficiency, pediatric HIV, a primary immunodeficiency, chronic inflammatory demyelinating polyneuropathy, adult HIV, Alzhemier's disease, autism, Behcet's disease, capillary leak syndrome, chronic fatigue syndrome, *Clostridium difficile* colitis, dermatomyositis and polymyositis, Grave's ophthalmopathy, muscular dystrophy, inclusion body myositis, infertility, Lambert-Eaton syndrome, Lennox-Gastaut, Lupus erythematosus, multifocal motor neuropathy, multiple sclerosis, myasthenia gravis, neonatal alloimmune thrombocytopenia, parvovirus B19, pemphigus, post-transfusion purpura, renal transplant rejection, spontaneous abortion/miscarriage, Sjogren's syndrome, stiff person syndrome, opsoclonus myoclonus, severe sepsis and septic shock, toxic epidermal necrolysis, multiple myeloma, Wegener's granulomatosis, Churg-Strauss syndrome, and acute infections relative to IgG (e.g., IVIG).

In some aspects, the present disclosure encompasses a preparation, e.g., a therapeutic preparation, that includes Fc-containing sialylated glycoproteins. In some aspects, a preparation, e.g., a therapeutic preparation, includes a mixture of a sialylated glycoproteins, monosialylated glycoproteins (e.g., monosialylated on an α1-3 arm of a branched glycan (e.g., with a NeuAc-α2,6-Gal terminal linkage), and/or disialylated glycoproteins (e.g., sialylated on both an α1-3 arm and an α1-6 arm of a branched glycan). In some embodiments, a preparation of glycoproteins includes at least about 75%, at least about 80%, at least about 85%, at least about 90%, at least about 95%, or about 100% glyco-proteins that are monosialylated on an α3 arm of a branched glycan (e.g., with a NeuAc-α2,6-Gal terminal linkage). In some embodiments, a preparation of glycoproteins includes less than about 25%, less than about 20%, less than about 15%, less than about 10%, less than about 5%, or less, a sialylated and/or disialylated glycoproteins. In some embodiments, an Fc-containing glycoprotein preparation is selected from a preparation of Fc fragments, a preparation of antibody molecules, a preparation of Fc-fusion proteins (e.g., Fc-receptor fusion proteins), and a preparation of IVIG.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIGS. 1A-1C show exemplary ST6Gal sialyltransferase sequences. FIG. 1A depicts an exemplary ST6Gal sialyltransferase amino acid sequence (SEQ ID NO:1). FIG. 1B depicts an exemplary ST6Gal sialyltransferase amino acid sequence (SEQ ID NO:2). FIG. 1C depicts an exemplary ST6 Gal sialyltransferase amino acid sequence (SEQ ID NO:3).

DETAILED DESCRIPTION

Figure 2:
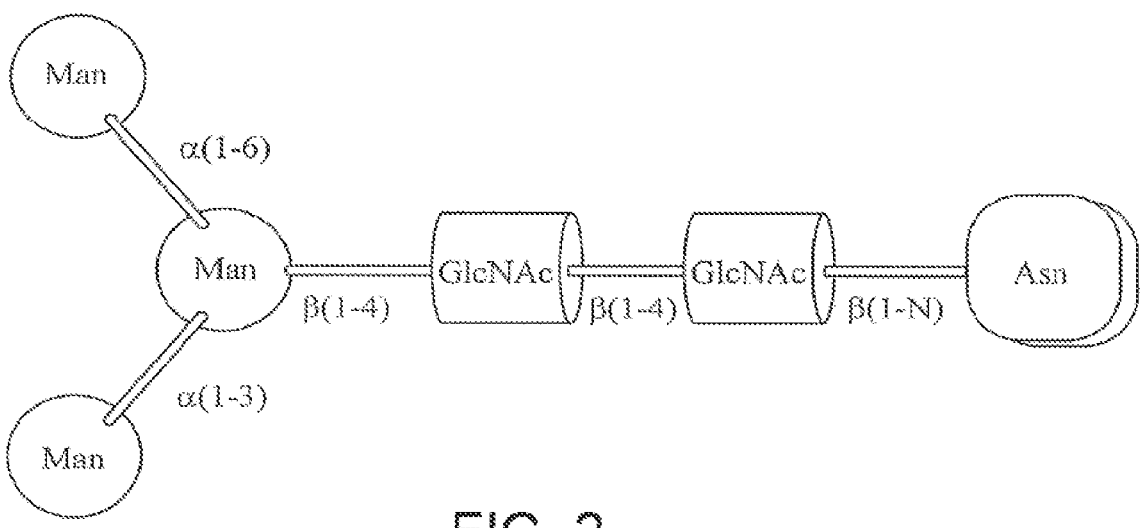
FIG. 2 is a schematic illustration of a common core pentasaccharide (Man)$_3$(GlcNAc)(GlcNAc) of N-glycans.

Antibodies are glycosylated at conserved positions in the constant regions of their heavy chain. For example, IgG antibodies have a single N-linked glycosylation site at Asn297 of the CH2 domain. Each antibody isotype has a distinct variety of N-linked carbohydrate structures in the constant regions. For human IgG, the core oligosaccharide normally consists of GlcNAc$_2$Man$_3$GlcNAc, with differing numbers of outer residues. Variation among individual IgGs can occur via attachment of galactose and/or galactose-sialic acid at one or both terminal GlcNAc or via attachment of a third GlcNAc arm (bisecting GlcNAc).

The inventors have discovered that glycoproteins having branched glycans that are preferentially sialylated on an α1,3 arm of the branched glycan in the Fc region (e.g., with a NeuAc-α2,6-Gal terminal linkage), have increased anti-inflammatory properties. Described herein are glycoproteins (e.g., antibodies or fusion proteins, such as Fc fusion proteins) having branched glycans sialylated on an α1,3 arm of the branched glycan in the Fc region (e.g., with a NeuAc-α2,6-Gal terminal linkage) and have increased anti-inflammatory activity relative to glycoproteins not having such sialylated glycans. Methods of making and using such compositions are also described.

Definitions

As used herein, the terms "approximately" or "about" as applied to one or more values of interest, refer to a value that is similar to a stated reference value. In some embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

As used herein, the term "equivalent" refers to a difference, for example, the percent of a particular glycoform in a glycoprotein preparation, that does not result in a difference in biological properties (e.g., potency, binding characteristics, stability, or susceptibility to degradation) as compared to a target glycoprotein preparation. In some instances, "equivalent" refers to the allowed difference of the percent of a particular glycoform in a glycoprotein preparation in a specification for commercial release of a drug product under Section 351(k) of the PHS Act.

As used herein, "glycan" is a sugar, which can be monomers or polymers of sugar residues, such as at least three sugars, and can be linear or branched (e.g., have an α 1,3 arm and an α 1,6 arm). A "glycan" can include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

As used herein, the term "glycoprotein" refers to a protein that contains a peptide backbone covalently linked to one or more sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. Glycoproteins can contain O-linked sugar moieties and/or N-linked sugar moieties.

As used herein, the term "glycoprotein preparation" refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

As used herein, the term "pharmaceutical preparation" refers to a preparation that comprises an active pharmaceutical ingredient or "API" in a dosage form suitable for human or veterinary use (e.g., a preparation in which glycoproteins are present at a concentration of at least 20 mg/mL).

As used herein, the term "pharmaceutical product" refers to a sterile preparation intended for human or veterinary use, formulated for use in a subject and presented in its finished dosage form (e.g., packaged for administration).

"Pharmaceutical preparations" and "pharmaceutical products" can be included in kits containing the preparation or product and instructions for use.

"Pharmaceutical preparations" and "pharmaceutical products" generally refer to compositions in which the final predetermined level of sialylation has been achieved. To that end, "pharmaceutical preparations" and "pharmaceutical products" are substantially free of ST6Gal sialyltransferase and/or sialic acid donor (e.g., cytidine 5'-monophospho-N-acetyl neuraminic acid) or the byproducts thereof (e.g., cytidine 5'-monophosphate).

"Pharmaceutical preparations" and "pharmaceutical products" are generally substantially free of other components of a cell in which the glycoproteins were produced (e.g., the endoplasmic reticulum or cytoplasmic proteins and RNA), if recombinant.

The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform".

"Reference glycoprotein", as used herein, refers to a glycoprotein having substantially the same amino acid sequence as (e.g., having about 90-100% identical amino acids of) a glycoprotein described herein, e.g., a glycoprotein to which it is compared. In some embodiments, a reference glycoprotein is a therapeutic glycoprotein described herein, e.g., an FDA approved therapeutic glycoprotein.

"Predetermined level," as used herein, refers to a prespecified particular level (e.g., an absolute value or range) of one or more particular glycans. In some embodiments, a predetermined level is a level of one or more particular glycans (e.g., branched glycans having a sialic acid on an α1-3 arm and/or branched glycans having a sialic acid on an α1-6 arm) in a preparation of a reference glycoprotein. In some embodiments, a predetermined level is expressed as a percent.

For any given parameter, in some embodiments, "percent" refers to the number of moles of a particular glycan (glycan X) relative to total moles of glycans of a preparation. In some embodiments, "percent" refers to the number of moles of PNGase F-released Fc glycan X relative to total moles of PNGase F-released Fc glycans detected.

By "purified" (or "isolated") refers to a nucleic acid sequence (e.g., a polynucleotide) or an amino acid sequence (e.g., a glycoprotein) that is removed or separated from other components present in its natural environment or substantially free of reactants or byproducts thereof used in its production. For example, a purified or isolated glycoprotein is one that is separated from other components of a cell in which it was produced (e.g., the endoplasmic reticulum or cytoplasmic proteins and RNA). A further example of a purified or isolated glycoprotein are sialylated glycoproteins which are substantially free of ST6Gal sialyltransferase and/or sialic acid donor (e.g., cytidine 5'-monophospho-N-acetyl neuraminic acid) or the byproducts thereof (e.g., cytidine 5'-monophosphate) used in their production. An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free from other components present in natural environment of the indicated nucleic acid sequence or amino acid sequence.

As used herein, "polynucleotide" (or "nucleotide sequence" or "nucleic acid molecule") refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, "polypeptide" (or "amino acid sequence" or "protein") refers to an oligopeptide, peptide, polypeptide, or protein sequence, and fragments or portions thereof, and to naturally occurring or synthetic molecules. "Amino acid sequence" and like terms, such as "polypeptide" or "protein", are not meant to limit the indicated amino acid sequence to the complete, native amino acid sequence associated with the recited protein molecule.

The articles "a" and "an" are used herein to refer to one or to more than one (i.e., to at least one) of the grammatical object of the article. By way of example, "an element" means one element or more than one element.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, to a degree detectable to one skilled in the art. An effective amount, manner, or mode can vary depending on the subject and may be tailored to the subject.

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

An "Fc region-containing glycoprotein" is a glycoprotein that includes all or a substantial portion of an Fc region. Examples of an Fc region-containing glycoprotein preparation include, e.g., a preparation of Fc fragments, a preparation of antibody molecules, a preparation of Fc-fusion proteins (e.g., an Fc-receptor fusion protein), and a preparation of pooled, polyvalent immunoglobulin molecules (e.g., IVIG). Such an Fc region-containing glycoprotein may be recombinant (e.g., a recombinant Fc fragment preparation or a recombinant antibody preparation) or naturally derived (such as IVIG).

As used herein, the term "Fc region variant" refers to an analog of an Fc region that possesses one or more Fc-mediated activities described herein. This term includes Fc regions comprising one or more amino acid modifications (e.g., substitutions, additions, or deletions) relative to a wild type or naturally existing Fc region. For example, variant Fc regions can possess at least about 50% homology, at least about 75% homology, at least about 80% homology, at least about 85% homology, at least about 90% homology, at least about 95% homology, or more, with a naturally existing Fc region. For example, variant Fc regions can possess between 1 and 5 amino acid substitutions, e.g., 1, 2, 3, 4 or 5 amino acid substitutions such as phenylalanine to alanine substitutions. Fc region variants also include Fc regions comprising one or more amino acid residues added to or deleted from the N- or C-terminus of a wild type Fc region.

As used herein, an "N-glycosylation site of an Fc polypeptide" refers to an amino acid residue within an Fc polypeptide to which a glycan is N-linked. In some embodiments, an Fc region contains a dimer of Fc polypeptides, and the Fc region comprises two N-glycosylation sites, one on each Fc polypeptide.

As used herein, the terms "coupled", "linked", "joined", "fused", and "fusion" are used interchangeably. These terms refer to the joining together of two more elements or components by whatever means, including chemical conjugation or recombinant means.

The terms "overexpress," "overexpression," or "overexpressed" interchangeably refer to a protein or nucleic acid that is transcribed or translated at a detectably greater level, such as in a cancer cell, in comparison to a control cell. The term includes expression due to transcription, post transcriptional processing, translation, post-translational processing, cellular localization (e.g., organelle, cytoplasm, nucleus, cell surface), and RNA and protein stability, as compared to a control cell. Overexpression can be detected using conventional techniques, e.g., for detecting mRNA (i.e., RT-PCR, PCR, hybridization) or proteins (i.e., ELISA, immunohistochemical techniques). Overexpression can be expression in an amount greater than about 10%, 20%, 30%, 40%, 50%, 60%, 70%, 80%, 90% or more compared to a control cell. In certain instances, overexpression is 1-fold, 2-fold, 3-fold, 4-fold, or more, higher level of transcription or translation compared to a control cell.

As used herein, the term "ST6Gal sialyltransferase" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in transfer of a sialic acid to a terminal galactose of a glycan through an α2,6 linkage (e.g., ST6 Gal-I). A wide variety of ST6Gal sialyltransferase sequences are known in the art. In some embodiments, the ST6Gal sialyltransferase has at least 70%, 75%, 80%, 85%, 90%, 91%, 92%, 93%, 94%, 95%, 96%, 97%, 98%, or 99% identity, or is 100% identical, to amino acid residues 95-416 of SEQ ID NO:1, to SEQ ID NO:2, or to SEQ ID NO:3 (FIGS. 1A-1C).

I. Glycoproteins

Glycoproteins include, for example, any of a variety of hematologic agents (including, for instance, erythropoietin, blood-clotting factors, etc.), interferons, colony stimulating factors, antibodies, enzymes, and hormones. The identity of a particular glycoprotein is not intended to limit the present disclosure, and any glycoprotein of interest can be a reference glycoprotein in the present methods.

A reference glycoprotein described herein can include a target-binding domain that binds to a target of interest (e.g., binds to an antigen). For example, a glycoprotein, such as an antibody, can bind to a transmembrane polypeptide (e.g., receptor) or ligand (e.g., a growth factor). Exemplary molecular targets (e.g., antigens) for glycoproteins described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2

(ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, ICAM-1, VCAM and αvβ3 integrin including either α or β subunits thereof (e.g., anti-CD11a, anti-CD18 or anti-CD11b antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemookine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Nonlimiting, exemplary reference glycoproteins that include an Fc region of an antibody heavy chain include abatacept (Orencia®, Bristol-Myers Squibb), abciximab (ReoPro®, Roche), adalimumab (Humira®, Bristol-Myers Squibb), alefacept (Amevive®, Astellas Pharma), alemtuzumab (Campath®, Genzyme/Bayer), basiliximab (Simulect®, Novartis), bevacizumab (Avastin®, Roche), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), ibritumomab (Zevalin®, Spectrum Pharmaceuticals), infliximab (Remicade®, Centocor), muromonab (Orthoclone OKT3®, Janssen-Cilag), natalizumab (Tysabri®, Biogen Idec, Elan), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tositumomab (Bexxar®, GlaxoSmithKline), and trastuzumab (Herceptin®, Roche).

A. N-Linked Glycosylation

N-linked oligosaccharide chains are added to a protein in the lumen of the endoplasmic reticulum (see Molecular Biology of the Cell, Garland Publishing, Inc. (Alberts et al., 1994)). Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains 3 glucose, 9 mannose, and 2 N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues (depicted in FIG. 2, linked to an asparagine residue). One of the branches is referred to in the art as the "α1,3 arm", and the second branch is referred to as the "α1,6 arm", as denoted in FIG. 2.

N-glycans can be subdivided into three distinct groups called "high mannose type", "hybrid type", and "complex type", with a common pentasaccharide core (Man (alpha1, 6)-(Man(alpha1,3))-Man(beta1,4)-GlcpNAc(beta 1,4)-GlcpNAc(beta 1,N)-Asn) occurring in all three groups.

After initial processing in the endoplasmic reticulum, the glycoprotein is transported to the Golgi where further processing may take place. If the glycan is transferred to the Golgi before it is completely trimmed to the core pentasaccharide structure, it results in a "high-mannose glycan".

Additionally or alternatively, one or more monosaccharides units of N-acetylglucosamine may be added to the core mannose subunits to form a "complex glycan". Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

Sialic acids are a family of 9-carbon monosaccharides with heterocyclic ring structures. They bear a negative charge via a carboxylic acid group attached to the ring as well as other chemical decorations including N-acetyl and N-glycolyl groups. The two main types of sialyl residues found in glycoproteins produced in mammalian expression systems are N-acetyl-neuraminic acid (NeuAc) and N-glycolylneuraminic acid (NeuGc). These usually occur as terminal structures attached to galactose (Gal) residues at the non-reducing termini of both N- and O-linked glycans. The glycosidic linkage configurations for these sialyl groups can be either α2,3 or α2,6.

N-Linked Glycosylation in Antibodies

Antibodies are glycosylated at conserved, N-linked glycosylation sites in the Fc regions of immunoglobulin heavy chains. For example, each heavy chain of an IgG antibody has a single N-linked glycosylation site at Asn297 of the CH2 domain (see Jefferis, Nature Reviews 8:226-234 (2009)). IgA antibodies have N-linked glycosylation sites within the CH2 and CH3 domains, IgE antibodies have N-linked glycosylation sites within the CH3 domain, and IgM antibodies have N-linked glycosylation sites within the CH1, CH2, CH3, and CH4 domains (see Arnold et al., J. Biol. Chem. 280:29080-29087 (2005); Mattu et al., J. Biol. Chem. 273:2260-2272 (1998); Nettleton et al., Int. Arch. Allergy Immunol. 107:328-329 (1995)).

Each antibody isotype has a distinct variety of N-linked carbohydrate structures in the constant regions. For example, IgG has a single N-linked biantennary carbohydrate at Asn297 of the CH2 domain in each Fc polypeptide of the Fc region, which also contains the binding sites for C1q and FcγR (see Jefferis et al., Immunol. Rev. 163:59-76 (1998); and Wright et al., Trends Biotech 15:26-32 (1997)). For human IgG, the core oligosaccharide normally consists of GlcNAc₂Man₃GlcNAc, with differing numbers of outer residues. Variation among individual IgG can occur via attachment of galactose and/or galactose-sialic acid at one or both terminal GlcNAc or via attachment of a third GlcNAc arm (bisecting GlcNAc).

B. Antibodies

Figure 3:
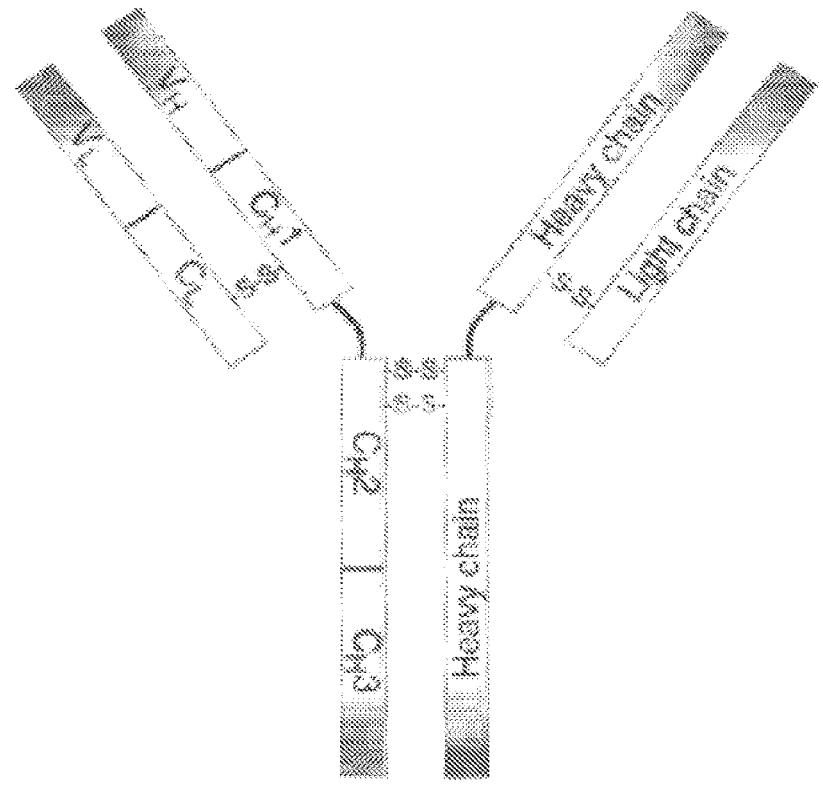
FIG. 3 is a schematic illustration of an IgG antibody molecule.

The basic structure of an IgG antibody is illustrated in FIG. 3. As shown in FIG. 3, an IgG antibody consists of two identical light polypeptide chains and two identical heavy polypeptide chains linked together by disulphide bonds. The first domain located at the amino terminus of each chain is variable in amino acid sequence, providing the antibody binding specificities found in each individual antibody. These are known as variable heavy (VH) and variable light (VL) regions. The other domains of each chain are relatively invariant in amino acid sequence and are known as constant heavy (CH) and constant light (CL) regions. As shown in FIG. 3, for an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment", as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')₂ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and the fragments can be screened for utility in the same manner as are intact antibodies.

Reference antibodies or fragments described herein can be produced by any method known in the art for the synthesis of antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using the methods described in, e.g., Morrison, 1985, Science 229:1202, and humanized antibodies by methods described in, e.g., U.S. Pat. No. 6,180,370.

Additional reference antibodies described herein are bispecific antibodies and multivalent antibodies, as described in, e.g., Segal et al., J. Immunol. Methods 248:1-6 (2001); and Tutt et al., J. Immunol. 147: 60 (1991).

Naturally derived antibodies that can be used in the methods of the invention include, for example intravenous immunoglobulin (IVIG) and polypeptides derived from IVIG (e.g., polypeptides purified from IVIG (e.g., enriched for sialylated IgGs), modified IVIG (e.g., IVIG IgGs enzymatically sialylated), or Fc regions of IVIG (e.g., papain digested and sialylated)).

IVIG is a blood product containing pooled, polyvalent IgG extracted from the plasma of over one thousand blood donors. IVIG is used in the treatment of rheumatoid arthritis, X-linked agammagloulinemia, hypogammaglobulinemia, an acquired compromised immunity condition, immune thrombocytopenia, Kawasaki disease, allogeniec bone marrow transplant, chronic lymphocytic leukemia, common variable immunodeficiency, pediatric HIV, a primary immunodeficiency, chronic inflammatory demyelinating polyneuropathy, adult HIV, Alzhemier's disease, autism, Behcet's disease, capillary leak syndrome, chronic fatigue syndrome, *Clostridium difficile* colitis, dermatomyositis and polymyositis, Grave's ophthalmopathy, muscular dystrophy, inclusion body myositis, infertility, Lambert-Eaton syndrome, Lennox-Gastaut, Lupus erythematosus, multifocal motor neuropathy, multiple sclerosis, myasthenia gravis, neonatal alloimmune thrombocytopenia, parvovirus B19, pemphigus, post-transfusion purpura, renal transplant rejection, spontaneous abortion/miscarriage, Sjogren's syndrome, stiff person syndrome, opsoclonus myoclonus, severe sepsis and septic shock, toxic epidermal necrolysis, multiple myeloma, Wegener's granulomatosis, Churg-Strauss syndrome, and acute infections.

C. Glycoprotein Conjugates

The disclosure includes glycoproteins (or Fc regions or Fc fragments containing one or more N-glycosylation sites thereof) that are conjugated or fused to one or more heterologous moieties and that have different levels of sialylated glycans relative to a corresponding reference glycoprotein. Heterologous moieties include, but are not limited to, peptides, polypeptides, proteins, fusion proteins, nucleic acid molecules, small molecules, mimetic agents, synthetic drugs, inorganic molecules, and organic molecules. In some instances, a reference glycoprotein is a fusion protein that comprises a peptide, polypeptide, protein scaffold, scFv, dsFv, diabody, Tandab, or an antibody mimetic fused to an Fc region, such as a glycosylated Fc region. The fusion protein can include a linker region connecting the Fc region to the heterologous moiety (see, e.g., Hallewell et al. (1989), J. Biol. Chem. 264, 5260-5268; Alfthan et al. (1995), Protein Eng. 8, 725-731; Robinson & Sauer (1996)).

Exemplary, nonlimiting reference fusion proteins include abatacept (Orencia®, Bristol-Myers Squibb), alefacept (Amevive®, Astellas Pharma), denileukin diftitox (Ontak®, Eisai), etanercept (Enbrel®, Amgen-Pfizer), and rilonacept (Arcalyst®, Regeneron Pharmaceuticals).

In some instances, a reference fusion protein includes an Fc region (or an Fc fragment containing one or more N-glycosylation sites thereof) conjugated to a heterologous polypeptide of at least 10, at least 20, at least 30, at least 40, at least 50, at least 60, at least 70, at least 80, at least 90 or at least 100 amino acids.

In some instances, a reference fusion protein can include an Fc region (or Fc fragment containing one or more N-glycosylation sites thereof) conjugated to marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, a reference glycoprotein (or an Fc region or Fc fragment containing one or more N-glycosylation sites thereof) is conjugated to a diagnostic or detectable agent. Such fusion proteins can be useful for monitoring or prognosing the development or progression of disease or disorder as part of a clinical testing procedure, such as determining the efficacy of a particular therapy. Such diagnosis and detection can be accomplished by coupling the glycoprotein to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin;

fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C), sulfur ($^{35}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{81}$F) $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn, and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

II. Sialylated Glycoproteins

Glycoproteins of the present disclosure have glycan compositions that are different from corresponding reference glycoproteins. For example, the present disclosure encompasses Fc region-containing glycoprotein preparations (e.g., IVIG, Fc or IgG antibodies) having higher levels of branched glycans that are sialylated on an α1-3 arm of the branched glycans in the Fc region (e.g., with a NeuAc-α2, 6-Gal terminal linkage), relative to a corresponding reference IgG antibody. The higher levels can be measured on an individual Fc region (e.g., an increase in the number of branched glycans that are sialylated on an α1-3 arm of the branched glycans in the Fc region), or the overall composition of a preparation of glycoproteins can be different (e.g., a preparation of glycoproteins can have a higher number or a higher percentage of branched glycans that are sialylated on an α1-3 arm of the branched glycans in the Fc region) relative to a corresponding preparation of reference glycoproteins).

In some embodiments, a nucleic acid encoding a reference Fc region-containing glycoprotein described herein is co-expressed in a host cell with one or more sialyltransferase enzymes, e.g., an α2,6 sialyltransferase (e.g., ST6Gal-1). Sialyltransferase enzymes are known in the art and are commercially available.

Methods and compositions described herein include the use of a sialyltransferase enzyme, e.g., an α2,6 sialyltransferase (e.g., ST6Gal-1). A number of ST6Gal sialyltransferases are known in the art and are commercially available (see, e.g., Takashima, Biosci. Biotechnol. Biochem. 72:1155-1167 (2008); Weinstein et al., J. Biol. Chem. 262: 17735-17743 (1987)). ST6Gal-I catalyzes the transfer of sialic acid from a sialic acid donor (e.g., cytidine 5'-mono-phospho-N-acetyl neuraminic acid) to a terminal galactose residue of glycans through an α2,6 linkage. The sialic acid donor reaction product is cytidine 5'-monophosphate.

In some embodiments, the disclosure encompasses methods of modifying activity of a sialyltransferase enzyme, e.g., a sialylating activity of a sialyltransferase enzyme. In some embodiments, activity is modified by expressing a sialyltransferase enzyme in eukaryotic cells (e.g., yeast, insect, or mammalian cells such as CHO cells), purifying the sialyl-transferase, and contacting the sialyltransferase with an Fc region-containing glycoprotein, thereby preferentially sialy-lating the α1,3 arms of branched glycans of the Fc region-containing glycoprotein. In some embodiments, such sialy-lated Fc region-containing glycoproteins exhibit anti-inflammatory activity.

In some embodiments, activity is modified by expressing a sialyltransferase enzyme in prokaryotic cells (e.g., bacterial cells, e.g., E. coli), purifying the sialyltransferase, and contacting the sialyltransferase with an Fc region-containing glycoprotein, thereby preferentially sialylating the α1,6 arms of branched glycans of the Fc region-containing glycoprotein. In some embodiments, such sialylated Fc region-containing glycoproteins do not exhibit anti-inflammatory activity.

In some embodiments, an Fc region-containing glycoprotein is co-expressed in a host cell with a sialyltransferase enzyme (e.g., ST6Gal sialyltransferase), and the enzyme sialylates a branched glycan as described herein.

In some embodiments, an Fc region-containing glycoprotein is expressed in a host cell, and the host cell endogenously expresses or recombinantly expresses a sialyltransferase (e.g., ST6Gal sialyltransferase). Additionally or alternatively, the host cell is cultured under conditions that increase the activity of a sialyltransferase (e.g., ST6Gal sialyltransferase) in the cell, thereby producing an Fc region-containing glycoprotein having branched glycans sialylated as described herein.

Recombinant expression of a gene, such as a nucleic acid encoding a reference glycoprotein and/or a sialyltransferase described herein, can include construction of an expression vector containing a polynucleotide that encodes a reference polypeptide and/or a sialyltransferase. Once a polynucleotide has been obtained, a vector for the production of the reference polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured using conventional techniques to produce reference polypeptides.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., E. coli and B. subtilis) transformed with recombinant bacteriophage DNA, plasmid DNA or cosmid DNA expression vectors containing polypeptide coding sequences; yeast (e.g., Saccharomyces and Pichia) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the *E. coli* expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by the inclusion of appropriate transcription enhancer elements, transcription terminators, etc. (see, e.g., Bittner et al., 1987, Methods in Enzymol. 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7030 and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

In some embodiments, a reference Fc region-containing glycoprotein is recombinantly produced in cells as described herein, purified, and contacted with a sialyltransferase enzyme in vitro to produce Fc region-containing glycoproteins containing higher levels of glycans having higher levels of sialic acid on the α1-3 arms of the branched glycans with a NeuAc-α2,6-Gal terminal linkage, relative to the reference glycoprotein. In some embodiments, a purified reference glycoprotein is contacted with the sialyltransferase in the presence of CMP-sialic acid, manganese, and/or other divalent metal ions.

A reference Fc region-containing glycoprotein can be purified by any method known in the art for purification, for example, by chromatography (e.g., ion exchange, affinity, and sizing column chromatography), centrifugation, differential solubility, or by any other standard technique for the purification of proteins. For example, a reference antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a reference glycoprotein can be fused to heterologous polypeptide sequences to facilitate purification.

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

In some embodiments, a glycoprotein can be purified using a lectin column by methods known in the art (see, e.g., WO 02/30954). For example, a preparation of glycoproteins can be enriched for glycoproteins containing glycans having sialic acids in α2,6 linkage as described in, e.g., WO2008/057634. Following enrichment of glycoproteins containing glycans having sialic acids in α2,6 linkage, the glycan composition of such glycoproteins can be further characterized to identify glycoproteins having sialic acids attached to the α1,3 arm of a branched glycan. Preparations of glycoproteins containing a predetermined level of glycans having sialic acids in α2,6 linkage on the α1,3 arm can be selected for use, e.g., for therapeutic use. Such compositions can have increased levels of anti-inflammatory activity.

In some embodiments, a glycoprotein, e.g., a glycosylated antibody, is sialylated after the glycoprotein is produced. For example, a glycoprotein can be recombinantly expressed in a host cell (as described herein) and purified using standard methods. The purified glycoprotein is then contacted with an ST6Gal sialyltransferase (e.g., a recombinantly expressed and purified ST6Gal sialyltransferase) in the presence of reaction conditions as described herein. In certain embodiments, the conditions include contacting the purified glycoprotein with an ST6Gal sialyltransferase in the presence of a sialic acid donor, e.g., cytidine 5'-monophospho-N-acetyl neuraminic acid, manganese, and/or other divalent metal ions. In some embodiments, IVIG is used in a sialylation method described herein.

In some embodiments, chemoenzymatic sialylation is used to sialylate glycoproteins. Briefly, this method involves sialylation of a purified branched glycan, followed by incorporation of the sialylated branched glycan en bloc onto a polypeptide to produce a sialylated glycoprotein.

A branched glycan can be synthesized de novo using standard techniques or can be obtained from a glycoprotein preparation (e.g., a recombinant glycoprotein, Fc, or IVIG) using an appropriate enzyme, such as an endoglycosidase (e.g., EndoH or EndoF). After sialylation of the branched glycan, the sialylated branched glycan can be conjugated to a polypeptide using an appropriate enzyme, such as a transglycosidase, to produce a sialylated glycoprotein.

In some embodiments, a branched glycan used in methods described herein is a galactosylated branched glycan (e.g., includes a terminal galactose residue). In some embodiments, a branched glycan is galactosylated before being sialylated using a method described herein. In some embodiments, a branched glycan is first contacted with a galactosyltransferase (e.g., a beta-1,3-galactosyltransferase) and subsequently contacted with an ST6Gal sialyltransferase as described herein. In some embodiments, a galactosylated glycan is purified before being contacted with an ST6Gal sialyltransferase. In some embodiments, a galactosylated glycan is not purified before being contacted with an ST6Gal sialyltransferase. In some embodiments, a branched glycan is contacted with a galactosyltransferase and an ST6Gal sialyltransferase in a single step.

Glycan compositions can be characterized using methods described in, e.g., Barb, Biochemistry 48:9705-9707 (2009); Anumula, J. Immunol. Methods 382:167-176 (2012); Gilar et al., Analytical Biochem. 417:80-88 (2011).

III. Glycan Evaluation

In some embodiments, glycans of glycoproteins are analyzed by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a glycoprotein preparation with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1 D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or glycoproteins. For example, in certain instances, glycans are analyzed in accordance with the present disclosure using one or more available methods (to give but a few examples, see Anumula, Anal. Biochem., 350(1):1, 2006; Klein et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995; WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof.

In some instances, methods for evaluating one or more target protein specific parameters, e.g., in a glycoprotein preparation, e.g., one or more of the parameters disclosed herein, can be performed by one or more of following methods.

In some instances, methods for evaluating one or more target protein specific parameters, e.g., in a glycoprotein preparation, e.g., one or more of the parameters disclosed herein, can be performed by one or more of following methods.

TABLE 1

| Exemplary methods of evaluating parameters: | | |
|---|---|---|
| Method(s) | Relevant literature | Parameter |
| C18 UPLC Mass Spec.* | Chen and Flynn, Anal. Biochem., 370:147-161 (2007) Chen and Flynn, J. Am. Soc. Mass Spectrom., 20:1821-1833 (2009) | Glycan(s) (e.g., N-linked glycan, exposed N-linked glycan, glycan detection, glycan identification, and characterization; site specific glycation; glycoform detection (e.g., parameters 1-7); percent glycosylation; and/or aglycoosyl) |
| Peptide LC-MS (reducing/non-reducing) | Dick et al., Biotechnol. Bioeng., 100:1132-1143 (2008) Yan et al., J. Chrom. A., 1164:153-161 (2007) Chelius et al., Anal. Chem., 78:2370-2376 (2006) Miller et al., J. Pharm. Sci., 100:2543-2550 (2011) | C-terminal lysine |
| LC-MS (reducing/non-reducing/alkylated) | Dick et al., Biotechnol. Bioeng., 100:1132-1143 (2008) Goetze et al., Glycobiol., 21:949-959 (2011) | |

TABLE 1-continued

| Exemplary methods of evaluating parameters: | | |
|---|---|---|
| Method(s) | Relevant literature | Parameter |
| Weak cation exchange (WCX) chromatography | Dick et al., Biotechnol. Bioeng., 100:1132-1143 (2008) | |
| LC-MS (reducing/non-reducing/alkylated) | Dick et al., Biotechnol. Bioeng., 100:1132-1143 (2008) Goetze et al., Glycobiol., 21:949-959 (2011) | N-terminal pyroglu |
| PeptideLC-MS (reducing/non-reducing) | Yan et al., J. Chrom. A., 1164:153-161 (2007) Chelius et al., Anal. Chem., 78:2370-2376 (2006) Miller et al., J. Pharm. Sci., 100:2543-2550 (2011) | |
| Peptide LC-MS (reducing/non-reducing) | Yan et al., J. Chrom. A., 1164:153-161 (2007); Xie et al., mAbs, 2:379-394 (2010) | Methionine oxidation |
| Peptide LC-MS (reducing/non-reducing) | Miller et al., J. Pharm. Sci., 100:2543-2550 (2011) | Site specific glycation |
| Peptide LC-MS (reducing/non-reducing) | Wang et al., Anal. Chem., 83:3133-3140 (2011); Chumsae et al., Anal. Chem., 81:6449-6457 (2009) | Free cysteine |
| Bioanalyzer (reducing/non-reducing)* | Forrer et al., Anal. Biochem., 334:81-88 (2004) | Glycan (e.g., N-linked glycan, exposed N-linked glycan) (including, for example, glycan detection, identification, and characterization; site specific glycation; glycoform detection; percent glycosylation; and/or aglycoosyl) |
| LC-MS (reducing/non-reducing/alkylated)* * Methods include removal (e.g., enzymatic, chemical, and physical) of glycans | Dick et al., Biotechnol. Bioeng., 100:1132-1143 (2008) Goetze et al., Glycobiol., 21:949-959 (2011) Xie et al., mAbs, 2:379-394 (2010) | Glycan (e.g., N-linked glycan, exposed N-linked glycan) (including, for example, glycan detection, identification, and characterization; site specific glycation; glycoform detection; aglycoosyl) percent glycosylation; and/or aglycoosyl) |
| Bioanalyzer (reducing/non-reducing) | Forrer et al., Anal. Biochem., 334:81-88 (2004) | Light chain : Heavy chain |
| Peptide LC-MS (reducing/non-reducing) | Yan et al., J. Chrom. A., 1164:153-161 (2007) Chelius et al., Anal. Chem., 78:2370-2376 (2006) Miller et al., J. Pharm. Sci., 100:2543-2550 (2011) | Non-glycosylation-related peptide modifications (including, for example, sequence analysis and identification of sequence variants; oxidation; succinimide; aspartic acid; and/or site-specific aspartic acid) |
| Weak cation exchange (WCX) chromatography | Dick et al., Biotechnol. Bioeng., 100:1132-1143 (2008) | Isoforms (including, for example, charge variants (acidic variants and basic variants); and/or deamidated variants) |
| Anion-exchange chromatography | Ahn et al., J. Chrom. B, 878:403-408 (2010) | Sialylated glycan |
| Anion-exchange chromatography | Ahn et al., J. Chrom. B, 878:403-408 (2010) | Sulfated glycan |
| 1,2-diamino-4,5-methylenedioxybenzene (DMB) labeling method | Hokke et al., FEBS Lett., 275:9-14 (1990) | Sialic acid |
| LC-MS | Johnson et al., Anal. Biochem., 360:75-83 (2007) | C-terminal amidation |
| LC-MS | Johnson et al., Anal. Biochem., 360:75-83 (2007) | N-terminal fragmentation |
| Circular dichroism spectroscopy | Harn et al., Current Trends in Monoclonal Antibody Development and Manufacturing, S. J. Shire et al., eds, 229-246 (2010) | Secondary structure (including, for example, alpha helix content and/or beta sheet content) |
| Intrinsic and/or ANS dye fluorescence | Harn et al., Current Trends in Monoclonal Antibody Development and Manufacturing, S. J. Shire et al., eds, 229-246 (2010) | Tertiary structure (including, for example, extent of protein folding) |

TABLE 1-continued

| Exemplary methods of evaluating parameters: | | |
| --- | --- | --- |
| Method(s) | Relevant literature | Parameter |
| Hydrogen-deuterium exchange-MS | Houde et al., Anal. Chem., 81:2644-2651 (2009) | Tertiary structure and dynamics (including, for example, accessibility f amide protons to solvent water) |
| Size-exclusion chromatography Analytical ultracentrifugation | Carpenter et al., J. Pharm. Sci., 99:2200-2208 (2010) Pekar and Sukumar, Anal. Biochem., 367:225-237 (2007) | Extent of aggregation |

The literature recited above are hereby incorporated by reference in their entirety or, in the alternative, to the extent that they pertain to one or more of the methods for determining a parameter described herein.

IV. Anti-Inflammatory Properties

The inventors have discovered that sialic acid-mediated anti-inflammatory properties on Fc-containing molecules are not only due to the level of sialylation, but due to particular branching arrangements. Accordingly, Fc region-containing glycoproteins described herein (e.g., Fc region-containing glycoproteins containing glycans containing sialic acid on α1,3 arms of branched glycans with a NeuAc-α2,6-Gal terminal linkage) have increased anti-inflammatory properties relative to a reference glycoprotein.

In some embodiments, Fc region-containing glycoproteins containing sialic acid on α1,3 arms of branched glycans with a NeuAc-α2,6-Gal terminal linkages exhibit increased anti-inflammatory activity relative to a reference glycoprotein, e.g., a level of anti-inflammatory activity that is at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, or higher, relative to a reference glycoprotein.

In some embodiment, Fc region-containing glycoproteins having sialic acids in both the α1,3 and α1,6 arms of branched glycans may inhibit anti-inflammatory activity of Fc-containing glycoproteins.

V. Pharmaceutical Compositions and Administration

A glycoprotein of the present disclosure (e.g., an Fc region-containing glycoprotein comprising branched glycans that are sialylated on an α1,3 arm of the branched glycan in the Fc region, e.g., with a NeuAc-α2,6-Gal terminal linkage), can be incorporated into a pharmaceutical composition and can exhibit anti-inflammatory activity. Such a pharmaceutical composition is useful as an improved composition for the prevention and/or treatment of diseases relative to the corresponding reference glycoprotein. Pharmaceutical compositions comprising a glycoprotein can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the sialylated glycoprotein with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some instances, the level of sialylated glycans (e.g., branched glycans that are sialylated on an α1,3 arm of the branched glycan in the Fc region, e.g., with a NeuAc-α2, 6-Gal terminal linkage) in a preparation of antibodies or Fc-containing polypeptides, produced using a method described herein can be compared to a predetermined level (e.g., a corresponding level in a reference standard), e.g., to make a decision regarding the composition of the polypeptide preparation, e.g., a decision to classify, select, accept or discard, release or withhold, process into a drug product, ship, move to a different location, formulate, label, package, release into commerce, or sell or offer for sale the polypeptide, e.g., a recombinant antibody. In other instances, the decision can be to accept, modify or reject a production parameter or parameters used to make the polypeptide, e.g., an antibody. Particular, nonlimiting examples of reference standards include a control level (e.g., a polypeptide produced by a different method) or a range or value in a product specification (e.g., an FDA label or Physician's Insert) or quality criterion for a pharmaceutical preparation containing the polypeptide preparation.

In some instances, methods (i.e., evaluation, identification, and production methods) include taking action (e.g., physical action) in response to the methods disclosed herein. For example, a polypeptide preparation is classified, selected, accepted or discarded, released or withheld, processed into a drug product, shipped, moved to a different location, formulated, labeled, packaged, released into commerce, or sold or offered for sale, depending on whether the preselected or target value is met. In some instances, processing may include formulating (e.g., combining with pharmaceutical excipients), packaging (e.g., in a syringe or vial), labeling, or shipping at least a portion of the polypeptide preparation. In some instances, processing includes formulating (e.g., combining with pharmaceutical excipients), packaging (e.g., in a syringe or vial), and labeling at least a portion of the preparation as a drug product described herein. Processing can include directing and/or contracting another party to process as described herein.

In some instances, a biological activity of a polypeptide preparation (e.g., an antibody preparation) is assessed. Biological activity of the preparation can be analyzed by any known method. In some embodiments, a binding activity of a polypeptide is assessed (e.g., binding to a receptor). In some embodiments, a therapeutic activity of a polypeptide is assessed (e.g., an activity of a polypeptide in decreasing severity or symptom of a disease or condition, or in delaying appearance of a symptom of a disease or condition). In some embodiments, a pharmacologic activity of a polypeptide is assessed (e.g., bioavailability, pharmacokinetics, pharmacodynamics). For methods of analyzing bioavailability, pharmacokinetics, and pharmacodynamics of glycoprotein therapeutics, see, e.g., Weiner et al., J. Pharm. Biomed. Anal. 15(5):571-9, 1997; Srinivas et al., J. Pharm. Sci. 85(1):1-4, 1996; and Srinivas et al., Pharm. Res. 14(7):911-6, 1997.

The particular biological activity or therapeutic activity that can be tested will vary depending on the particular polypeptide (e.g., antibody). The potential adverse activity or toxicity (e.g., propensity to cause hypertension, allergic reactions, thrombotic events, seizures, or other adverse events) of polypeptide preparations can be analyzed by any available method. In some embodiments, immunogenicity of a polypeptide preparation is assessed, e.g., by determining whether the preparation elicits an antibody response in a subject.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a modified glycoprotein can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

Example 1—Sialylation of Fc Molecules

Fc molecules were obtained or produced from various sources, glycan compositions were characterized, and anti-inflammatory activities were determined. The Fc molecules were tested for their ability to protect mice from joint inflammation in a mouse arthritis model using a method described in Anthony, Proc. Natl. Acad. Sci. U.S.A. 105: 19571-19578 (2008).

Fc molecules were derived from IVIG as follows. Commercial grade IVIG was buffer exchanged in to phosphate buffered saline (PBS) from its formulation buffer. This buffer exchanged IVIG was digested by papain at 37° C. using 5 g papain/mg of IVIG, and the digestion was quenched with iodoacetamide. The undigested IgG and Fc/Fab monomers were separated by size exclusion chromatography. The Fc/Fab peak was further purified on a Protein A column to remove the Fab fragments. The purified Fc was concentrated before performing the sialylation reaction.

Sialylation of the Fc or IVIG substrate was performed as follows. The substrate (75 mg/mL) was incubated at 37° C. for 24-48 hours with 50 mM UDP-galactose and 20 mU of bovine milk beta-1,4-galactosyltransferase per mg of substrate. The galactosylated substrate was further incubated at 37° C. for 48-72 hours with 80 mM CMP-sialic Acid and the specified number of units of alpha-2,6-sialyltransferase per mg of substrate for sialylation. Enzyme activity was determined as described in Anumula, Glycobiol. 22:912-917 (2012).

Figure 4:
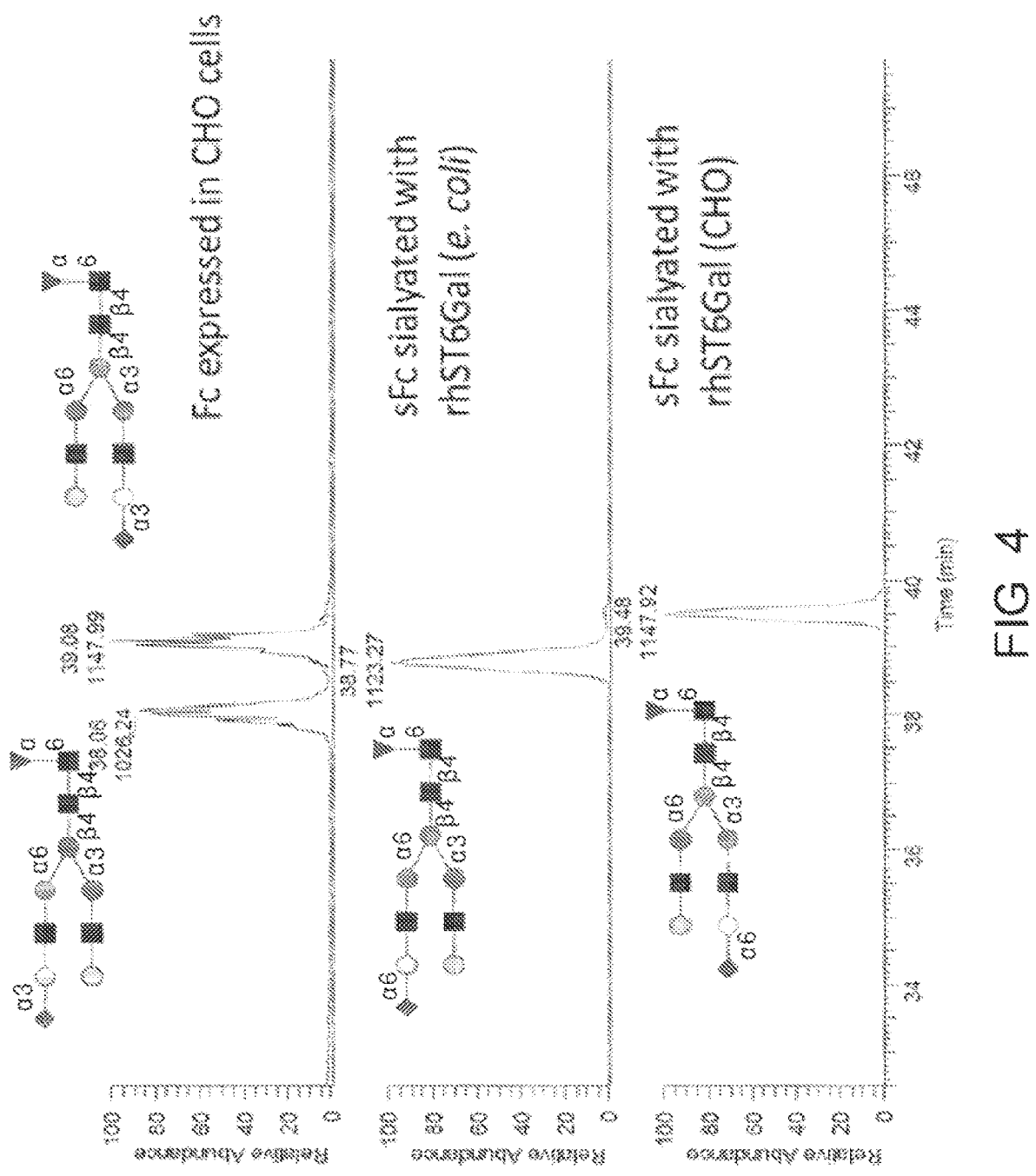
FIG. 4 a panel of representations of HILIC-LC extracted ion chromatogram of Fc glycopeptides expressed in CHO cells, glycopeptides derived from a sialylated Fc that was sialylated using a rhST6Gal expressed in E. coli cells, or glycopeptides derived from a sialylated Fc that was sialylated using a rhST6Gal expressed in CHO cells.

In another method, Fc was recombinantly expressed in and purified from CHO cells, and was subsequently sialylated using a recombinant sialyltransferase enzyme. The glycoprotein contained branched glycans having higher levels of sialic acid on the α1-3 arm of the branched glycans with a NeuAc-α2,6-Gal terminal linkage, relative to the reference glycoprotein. As depicted in FIG. 4 (top panel), Fc recombinantly expressed in CHO cells contained sialic acids linked to galactose in α2,3 linkage that were attached to both the α1,3 and α1,6 arms of the branched glycans.

Interestingly, Fc that was derived from IVIG and sialylated using human ST6Gal sialyltransferase enzyme (expressed in and purified from E. coli cells, 6.5 mU enzyme/mg of substrate) contained sialic acids linked to galactose in α2,6 linkage that were preferentially attached to the α1,6 arms of the branched glycans (FIG. 4, middle panel). When assayed in the mouse model of inflammation, these Fc molecules did not exhibit anti-inflammatory activity.

Surprisingly, when Fc that was derived from IVIG and sialylated using human ST6Gal sialyltransferase enzyme (expressed in and purified from CHO cells, 0.26 mU enzyme/mg of substrate), the Fcs contained sialic acids were linked to galactose in α2,6 linkage that were preferentially attached to the α1,3 arms of the branched glycans (FIG. 4, bottom panel). When assayed in the mouse model of inflammation, these Fc molecules exhibited anti-inflammatory activity.

In another exemplary method, a preparation of IVIG was obtained, and glycan composition was determined. About 5% to about 20% of the total glycans in the IVIG preparation contained one sialic acid on each glycan (i.e., were mono-sialylated). Further, greater than about 90% of these mono-sialylated glycans contained a sialic acid on an α1,3 arm of the branched glycans with a NeuAc-α2,6-Gal terminal linkage.

In another method, Fc molecules from IVIG were sialylated with human ST6Gal sialyltransferase (recombinantly expressed in and purified from insect cells, 0.42 mU enzyme/mg of substrate). The sialyltransferase preferentially sialylated the α1,3 arms of the branched glycans. These Fc molecules exhibit anti-inflammatory activity in the mouse model of inflammation.

---

The invention claimed is:

1. A method of producing a pharmaceutical preparation comprising an α1-3 sialylated Fc region-containing glycoprotein, wherein branched glycans on the Fc region are selectively sialylated on the α1-3 arm preferential to the α1-6 arm, the method comprising:

(a) contacting, in vitro, with a recombinant human beta-galactoside α2,6-sialyltransferase I (ST6Gal-I) enzyme expressed in and purified from a eukaryotic cell, a preparation comprising an Fc region-containing glycoprotein under conditions suitable for sialylation of the α1-3 arm branched glycans by the ST6Gal-I enzyme, forming the α1-3 sialylated Fc region-containing glycoprotein; and (b) processing the α1-3 sialylated Fc region-containing glycoprotein preparation into the pharmaceutical preparation, thereby producing the pharmaceutical preparation comprising an α1-3 sialylated Fc region-containing glycoprotein, wherein the branched glycans on the Fc region are selectively sialylated on the α1-3 arm, wherein the preparation comprising the Fc region-containing glycoprotein is immunoglobulin G (IgG) isolated from blood plasma.

2. The method of claim 1, wherein at least 95% of the α1-3 sialylated Fc region-containing glycoproteins have a sialic acid on the α1-3 arm of the branched glycans on the Fc region.

3. A method of increasing anti-inflammatory effect of a reference Fc region-containing glycoprotein preparation, comprising:

(a) contacting, in vitro, the reference Fc region-containing glycoprotein preparation with a recombinant human beta-galactoside α2,6-sialyltransferase 1 (ST6Gal-I) enzyme expressed in a eukaryotic cell, and a donor of sialic acid under conditions appropriate to selectively sialylate an α1-3 arm preferential to an α1-6 arm of a branched glycan of the Fc region, preparing an α1-3 sialylated Fc region-containing glycoprotein preparation, wherein the α1-3 sialylated glycoprotein preparation has the increased level of anti-inflammatory activity relative to the level of anti-inflammatory activity of the reference glycoprotein preparation, wherein the preparation comprising the Fc region containing glycoprotein is immunoglobulin G (IgG) isolated from blood plasma.

4. The method of claim 3, further comprising: (b) measuring α1-3 and/or α1-6 sialic acid content in the α1-3 sialylated Fc region-containing glycoprotein preparation.

5. The method of claim 1, wherein the branched glycans on the Fc are selectively sialylated on the α1-3 arm at a level of at least about 50% of the branched glycans having a having a sialic acid on the α1,3 arm and less than about 40% of the branched glycans having a sialic acid on the α1,6 arm.

6. The method of claim 1, wherein the recombinant ST6Gal-1 enzyme comprises an amino acid sequence with at least 80% identity to amino acid residues 95-416 of SEQ ID NO:1, SEQ ID NO:2, or SEQ ID NO:3.

7. The method of claim 1, wherein the eukaryotic cell is a CHO cell or an insect cell.

8. The method of claim 1, wherein the preparation comprising an Fc region-containing glycoprotein is contacted with 0.26 to 0.42 mU of the recombinant ST6Gal-1 enzyme per mg of Fc region-containing glycoprotein.

9. The method of claim 1, wherein the preparation comprising the α1-3 sialylated glycoprotein has a level of anti-inflammatory activity that is at least 10% higher than the level of anti-inflammatory activity of the reference glycoprotein preparation.

10. The method of claim 3, wherein at least 95% of the α1-3 sialylated Fc region-containing glycoproteins have a sialic acid on the α1-3 arm of the branched glycans on the Fc region.

11. The method of claim 3, wherein the branched glycans on the Fc are selectively sialylated on the $\alpha 1$-3 arm at a level of at least about 50% of the branched glycans having a having a sialic acid on the $\alpha 1$,3 arm and less than about 40% of the branched glycans having a sialic acid on the $\alpha 1$,6 arm.

12. The method of claim 3, wherein the recombinant ST6Gal-1 enzyme comprises an amino acid sequence with at least 80% identity to amino acid residues 95-416 of SEQ ID NO:1, SEQ ID NO:2, or SEQ ID NO:3.

13. The method of claim 3, wherein the eukaryotic cell is a CHO cell or an insect cell.

14. The method of claim 3, wherein the preparation comprising an Fc region-containing glycoprotein is contacted with 0.26 to 0.42 mU of the recombinant ST6Gal-1 enzyme per mg of Fc region-containing glycoprotein.

15. The method of claim 3, wherein the preparation comprising the $\alpha 1$-3 sialylated glycoprotein has a level of anti-inflammatory activity that is at least 10% higher than the level of anti-inflammatory activity of the reference glycoprotein preparation.

\* \* \* \* \*